US009216171B2

(12) United States Patent
Jones et al.

(10) Patent No.: US 9,216,171 B2
(45) Date of Patent: *Dec. 22, 2015

(54) METHODS OF PREVENTING ISCHEMIC INJURY USING PERIPHERAL NOCICEPTIVE STIMULATION

(75) Inventors: W. Keith Jones, Fort Thomas, KY (US); Xiaoping Ren, Mason, OH (US); Neal Lee Weintraub, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 770 days.

This patent is subject to a terminal disclaimer.

(21) Appl. No.: 12/800,109

(22) Filed: May 7, 2010

(65) Prior Publication Data

US 2010/0292755 A1 Nov. 18, 2010

Related U.S. Application Data

(60) Provisional application No. 61/215,616, filed on May 7, 2009, provisional application No. 61/339,159, filed on Mar. 1, 2010.

(51) Int. Cl.
*A61N 1/05* (2006.01)
*A61K 31/44* (2006.01)
*A61K 9/00* (2006.01)

(52) U.S. Cl.
CPC ............... *A61K 31/44* (2013.01); *A61K 9/0014* (2013.01)

(58) Field of Classification Search
CPC ...................................................... A61K 31/44
USPC ........................................................ 607/4, 14
See application file for complete search history.

(56) References Cited

U.S. PATENT DOCUMENTS

| 5,021,450 A | 6/1991 | Blumberg |
| 5,290,678 A | 3/1994 | Jackowski |
| 5,431,914 A | 7/1995 | Adekunle et al. |
| 5,962,532 A | 10/1999 | Campbell et al. |

(Continued)

FOREIGN PATENT DOCUMENTS

| EP | 2427056 | 3/2012 |
| EP | 10772869 | 7/2012 |

(Continued)

OTHER PUBLICATIONS

Ambardar et al. "Abdominal Wall Dimensions and Umbilical Position Vary Widely with BMI and Should be Taken into Account when Choosing Port Locations." Surgical Endoscopy. (2009) 23: 1995-2000.*

(Continued)

*Primary Examiner* — Carl H Layno
*Assistant Examiner* — Jennifer Ghand
(74) *Attorney, Agent, or Firm* — Dinsmore & Shohl LLP

(57) ABSTRACT

Methods of inhibiting ischemia-related and ischemia-reperfusion-related injury are provided. Remote administration of a C-fiber activator or TRPV1 agonist or remote electrical stimulation and activation of TRPV1 reduces ischemia-related tissue damage in subjects at risk for ischemia-related tissue damage. In aspects of the invention, remote application of a TRPV1 agonist inhibits ischemia-related cardiac tissue damage. Methods of inhibiting cardiac tissue damage by topically administering the TRPV1 agonist, capsaicin are provided.

5 Claims, 17 Drawing Sheets
(3 of 17 Drawing Sheet(s) Filed in Color)

(56) References Cited

U.S. PATENT DOCUMENTS

| | | | |
|---|---|---|---|
| 5,968,527 | A | 10/1999 | Litovitz |
| 6,277,398 | B1 | 8/2001 | Caruso |
| 6,463,327 | B1 * | 10/2002 | Lurie et al. ............. 607/42 |
| 7,149,574 | B2 | 12/2006 | Yun et al. |
| 7,218,964 | B2 | 5/2007 | Hill et al. |
| 7,482,469 | B2 | 1/2009 | Palin et al. |
| 7,630,760 | B2 | 12/2009 | Libbus et al. |
| 7,769,441 | B2 | 8/2010 | Foreman |
| 8,219,192 | B2 * | 7/2012 | Shuros et al. ............. 607/4 |
| 2003/0004549 | A1 | 1/2003 | Hill et al. |
| 2003/0100924 | A1 | 5/2003 | Foreman et al. |
| 2005/0090557 | A1 | 4/2005 | Muhammad et al. |
| 2005/0215533 | A1 | 9/2005 | Gottlieb et al. |
| 2006/0111745 | A1 | 5/2006 | Foreman et al. |
| 2006/0111746 | A1 | 5/2006 | Foreman et al. |
| 2006/0148903 | A1 | 7/2006 | Burch et al. |
| 2006/0178703 | A1 | 8/2006 | Huston et al. |
| 2006/0194805 | A1 | 8/2006 | Bakthavatchalam et al. |
| 2007/0036876 | A1 | 2/2007 | Burch et al. |
| 2007/0191895 | A1 | 8/2007 | Foreman et al. |
| 2007/0276453 | A1 | 11/2007 | Hill et al. |
| 2008/0051454 | A1 | 2/2008 | Wang |
| 2008/0058362 | A1 | 3/2008 | Singh et al. |
| 2008/0147143 | A1 * | 6/2008 | Popovic et al. ............. 607/48 |
| 2008/0262091 | A1 | 10/2008 | Burch et al. |
| 2009/0042946 | A1 | 2/2009 | Moore et al. |
| 2009/0318986 | A1 | 12/2009 | Alo et al. |
| 2010/0290998 | A1 * | 11/2010 | Jones et al. ............. 424/9.3 |

FOREIGN PATENT DOCUMENTS

| | | |
|---|---|---|
| SU | 1715351 | 2/1992 |
| WO | WO 2007/105210 A2 | 9/2007 |
| WO | WO2007/124169 A2 | 11/2007 |
| WO | PCT/US2010/033993 | 7/2010 |
| WO | PCT/US2010/033993 | 9/2010 |
| WO | WO2010/129845 A1 | 11/2010 |
| WO | PCT/US10/55695 | 3/2011 |
| WO | WO 2012/060845 A1 | 5/2012 |

OTHER PUBLICATIONS

Kallner, G., "Release and effects of calcitonin gene-related peptide in myocardial ischaemia", Scand. Cardiovasc. J. Suppl., 1998, p. 1-35, v. 49.

Jones et al, "Peripheral Nociception Associated with Surgical Incision Elicits Remote Nonischemic Cardioprotection via Neurogenic Activation of Protein Kinase C Signaling" Circulation, 2009, S1-S9, 120 [suppl 1], American Heart Association.

Gunthorpe & Szallasi, "Peripheral TRPV1 Receptors as Targets for Drug Development: New Molecules and Mechanisms", Current Pharmaceutical Design, 2008, 32-41, v.14.

Hu et al, "Involvement of capsaicin-sensitive sensory nerves in cardioprotection of rutaecarpine in rats", Regulatory Peptides, 2003, 45-49, 114.

Szallasi & Blumberg, "Vanilloid (Capsaicin) Receptors and Mechanisms", Pharmacological Reviews, 1999, 159-211, v 51-2.

Neeper et al, "Activation Properties of Heterologously Expressed Mammalian TRPV2", J. Biol. Chem. Mar. 29, 2007, p. 15894-15902, v.282-21.

Unknown, Capsaicin Technical Fact Sheet, National Pesticide Information Center, p. 1-11. [date unknown but prior to May 7, 2009].

Darwin, Mike, "The Pathophysiology of Ischemic Injury", Biopreservation Inc, 1995, c 2008 Alcor Life Extention Foundation (19 pgs).

Tang et al, "Involvement of capsaicin-sensitive sensory nerves in early and delayed cardioprotection induced by a brief ischaemia of the small intestine", Naun.Arch. Pharmacol, 1999, 243-247, v. 359.

Anson, Lesley, "Channelled Pain", Nature, Nov. 9, 2006, p. 156, v.444.

Gharat &Szallasi, "Advances in the design and therapeutic use of capsaicin receptor TRPV1 agonists and antagonists", Expert Opin. Ther. Patents, 2008, p. 159-209, v.18-2.

Chanda et al, "In Vitro Hepatic and Skin Metabolism of Capsaicin", Drug Metabolism & Deposition, 2008, 670-675, v. 36-4.

Mandadi & Roufogalis, "ThermoTRP Channels in Nociceptors: Taking a Lead from Capsaicin Receptor TRPV1", Current Neuropharmacology, 2008, p. 21-38, v. 6.

Guo et al, "Demonstration of an early and a late phase of ischemic preconditioning in mice", Am. M. Physiolol, 1998, H1375-H1387, v. 275.

Stotz et al, "Citral Sensing by TRANSient Receptor Potential Channels in Dorsal Root Ganglion Neurons", PLoS ONE, May 7, 2008, e.2082, v. 3-5.

Ren et al, "TNF-alpha is Required for Late Ischemic Preconditioning but not for Remote Preconditioning of Trauma", J. Surgical Research, 2004, p. 120-129, v.121.

Siemens et al, "Spider toxins activate the capsaicin receptor to produce inflammatory pain", Nature, Nov. 9, 2006, p. 208-212, v. 444, w/Supplementary Information.

Cromer & McIntyre, "Painful toxins acting at TRPV1", Toxicon, Oct. 26, 2007, p. 163-173, v. 51.

Starowicz et al, "TRPV1 Receptors in the Central Nervous System: Potential for Previously Unforeseen Therapeutic Applications", Current Pharma Design, 2008, p. 42-54, v.14.

Vivaldi et al, "Triphenyltetrazolium Staining of Irreversible Ischemic Injury Following Coronary Artery Occlusion in Rats", Am. J. Pathol., 1985, p. 522-530, v. 121-3.

Weintraub, Neal, A Randomized, Placebo-Controlled, Cross-Over Study to Assess the Safety and Efficacy of TOPical CAPsaicin in subjects with Stable Angina (TOPCAP), Initial INDA [date unknown but prior to May 7, 2010].

Fragrasso et al, "Nitric-Oxide Mediated Effects of Transdermal Capsaicin Patches on the Ischemic Threshold in Patients with Stable Coronary Disease", J. Cardiovasc. Pharmacol, Sep. 2004, p. 340-347, v. 44.

Tsou et al, "Electroacupuncture on PC6 (Neiguan) Attenuates Ischemia/Reperfusion Injury in Rat Hearts", Am. J. of Chinese Medicine, 2004, p. 951-965, v.32-6.

Gao et al, "A Preliminary Study on the Cardioprotection of Acupuncture Pretreatment in Rats with Ischemia and Reperfusion: Involvement of Cardiac beta-adrenoceptors", J. Physiol. Sci, Aug. 2004, p. 275-279, v. 56:4.

Gao et al, "Acupuncture pretreatment protects heart from injury in rats with myocardial ischemia and reperfusion via inhibition of the beta1-adrenoceptor signaling pathway", Life Sciences, 2007, p. 1484-1489, v. 80.

Strecker et al, "Release of Calcitonin gene-related peptide from the isolated mouse heart: Methodological validation of a new model", Neuropeptides, Jan. 18, 2006, 107-113, v. 40.

Wang & Wang, "TRPV1 Gene Knockout Impairs Postischemic Recovery in Isolated Perfused Heart in Mice", Circulation, Nov. 28, 2005, p. 3617-3623, v. 112.

Sexton et al, "12-Lipoxygenase-derived eicosanoids protect against myocardial ischemia/reperfusion injury via activation of neuronal TRPV1", FASEB Journal, Sep. 2007, p. 2695-2703, v. 21.

Lujan et al, "Electroacupuncture decreases the susceptibility to ventricular tachycardia in conscious rats by reducing cardiac metabolic demand", Am. J. Physiol. Heart Circ. Physiol., Jan. 5, 2007, p. H2550-2555, v.292.

Immke et al, "The TRPV1 receptor and nociception", Seminars in Cell & Developmental Biology, Sep. 24, 2006, p. 582-591, v. 17.

Ventura, "CAM and Cell Fate Targeting:Molecular and Energetic Insights into Cell Growth & Differentiation", Jul. 20, 2005, eCAM, Oxford University Press, p. 277-283, v. 2-3.

Ren et al, "Nociceptive Stimulation: A Novel Cardioprotective Strategy", Abstract 2317, Circulation 2008, S_705, v.118.

Zhou et al, "Early and delayed protection by capsaicin against reperfusion injury in rat hearts", Zhonggue Yao Li Xue Bao, Oct. 1999, 912-916, v. 10.

Skogvall et al, "Discovery of a potent and long-acting bronchorelaxing capsazepinoid Respir 4-95", Pulmonol. Pharmacol. & Therap., 2008, 125-133, v. 21.

(56) References Cited

OTHER PUBLICATIONS

Tsou et al, "Proteomic analysis finds different myocardial protective mechanisms fro median nerve stimulation by electroacupuncture and by local somatothermal stimulation", Intl J. of Molecular Medicine, 2004, 553-563, v. 14(4).

Jansco et al, "Direct Evidence for Neurogenic Inflammation and Its Prevention by Denervation and by Pretreatment with Capsaicin", Br. J. Pharmac. Chemother. (1967), 31, 138-151, Medical University Szeged, Szeged, Hungary.

Denet et al, "Skin electroporation for transdermal and topical delivery", Advanced Drug Delivery Reviews 56 (2004) 659-674, c 2004 Elsevier B.V., Belgium.

Fragasso et al., "Nitric-Oxide Mediated Effects of Transdermal Capsaicin Patches on the Ischemic Threshold in Patents with Stable Coronary Disease", J. Cardiovasc Pharmacol, Sep. 2004, p. 340-347, vol. 44, No. 3.

Zhong et al., "N-oleoyldopamine, a novel endogenous capsaicin-like lipid, protects the heart against ischemia-reperfusion injury via activation of TRPV1", Am J. Physiol Heart Circ Physiol, Aug. 2008, p. H728-H735, vol. 295, American Physiological Society, US.

* cited by examiner

FIG. 1A(1)
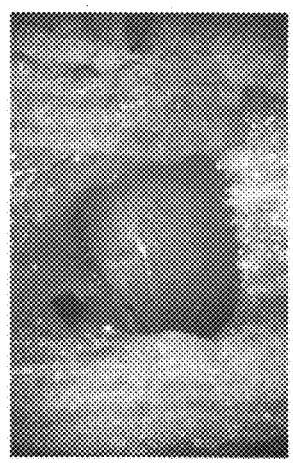
FIG. 1A(2)
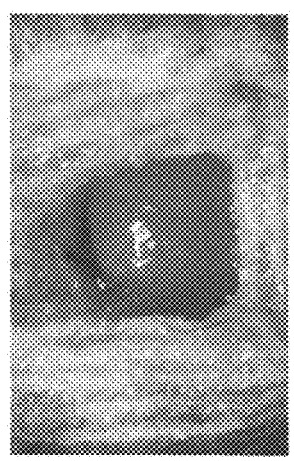
FIG. 1A(3)
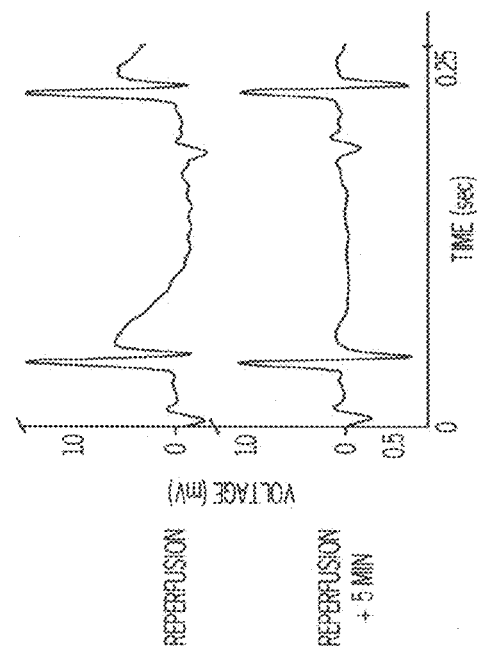
FIG. 1A(4)
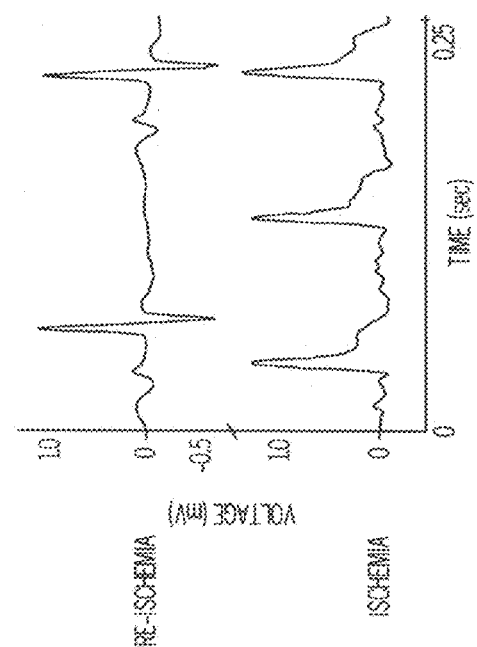
FIG. 1A(5)

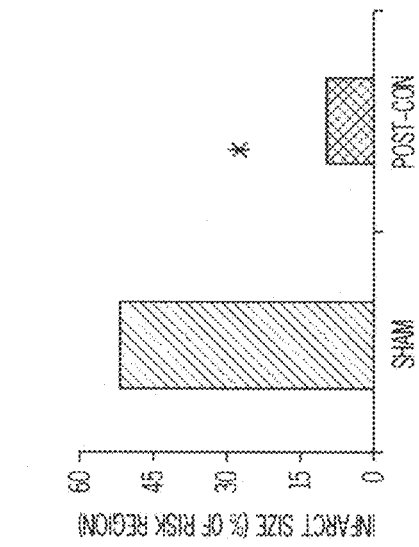
FIG. 1B(1) ANS-PC
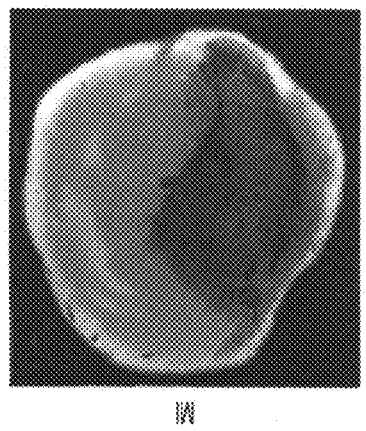
FIG. 1B(2) SHAM CONTROL
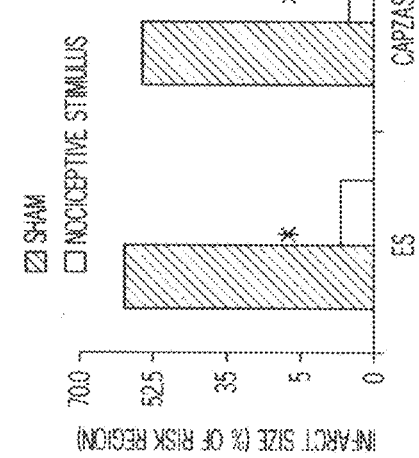
FIG. 1C
FIG. 1D

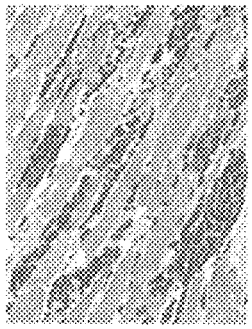 FIG. 1E(1)
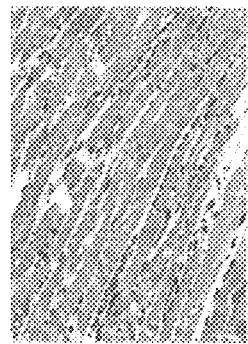 FIG. 1E(2)
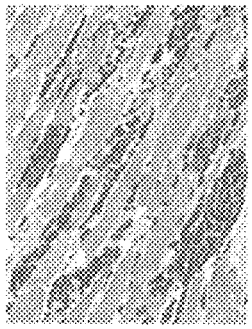 FIG. 1E(3)
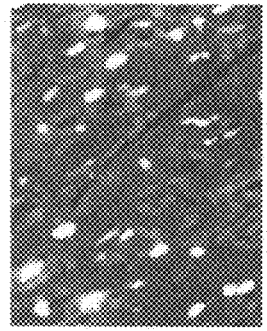 FIG. 1F(1)
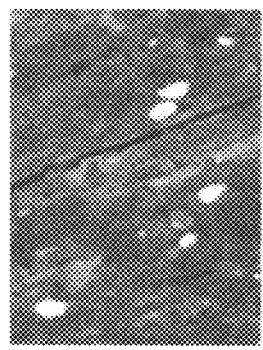 FIG. 1F(2)
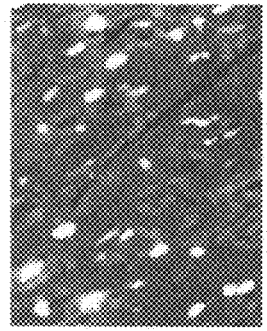 FIG. 1F(3)

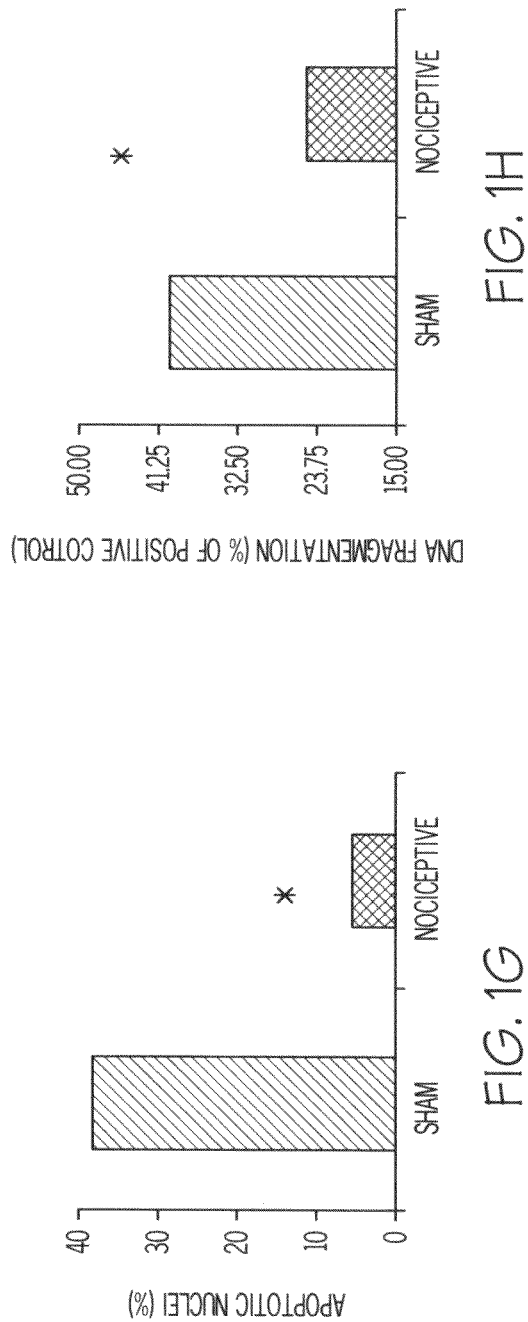

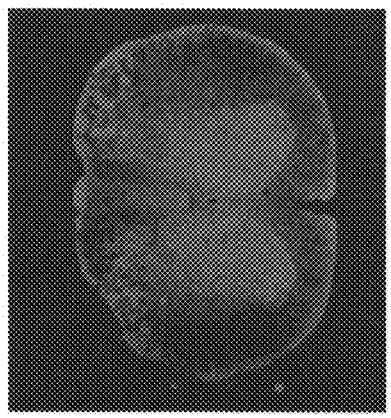
FIG. 2C(2)
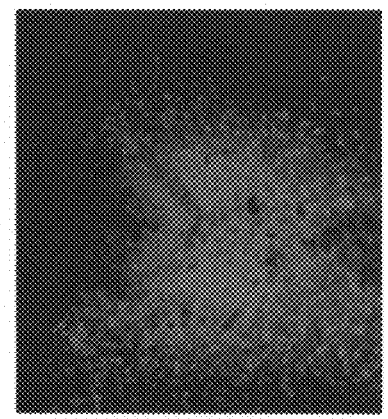
FIG. 2C(5)
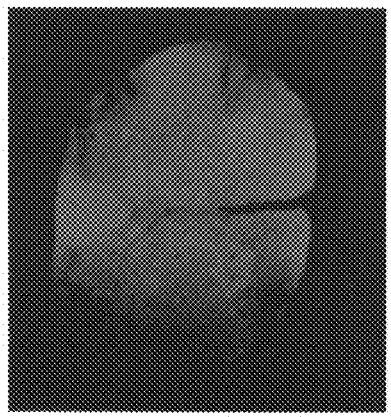
FIG. 2C(3)
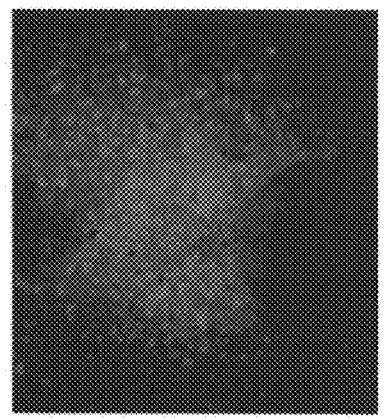
FIG. 2C(6)
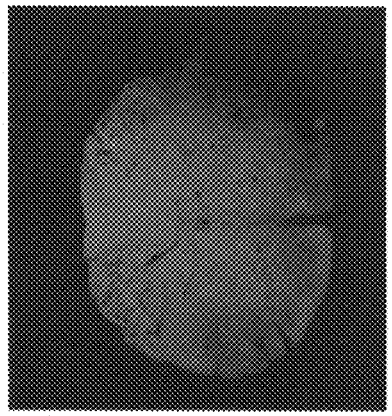
FIG. 2C(1)
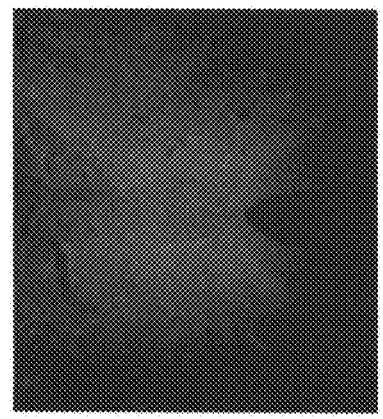
FIG. 2C(4)

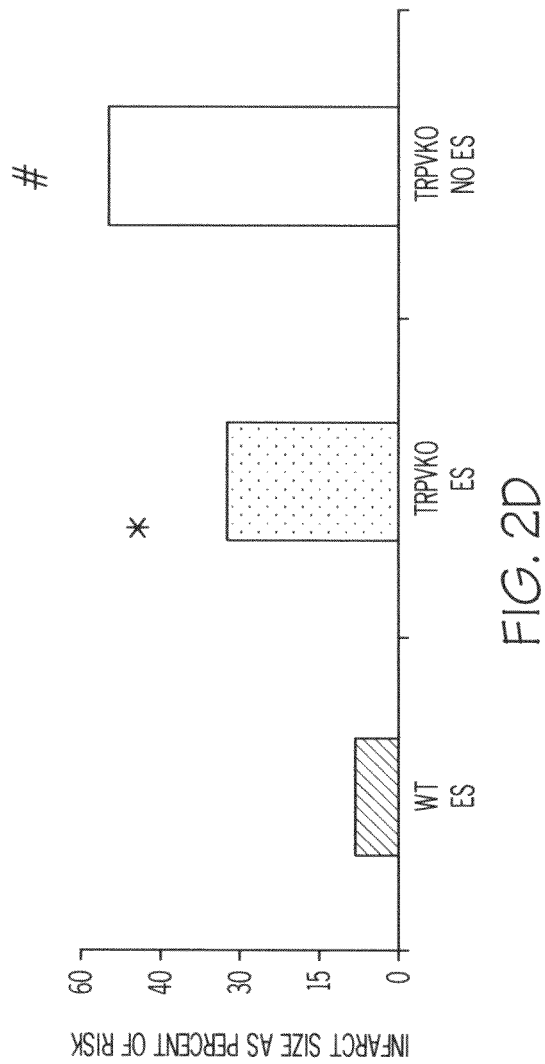
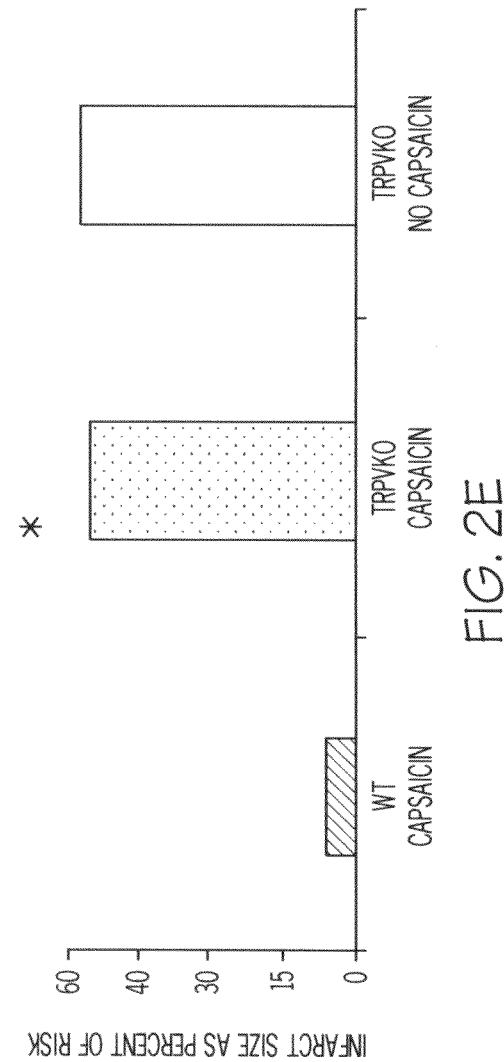
FIG. 2D
FIG. 2E

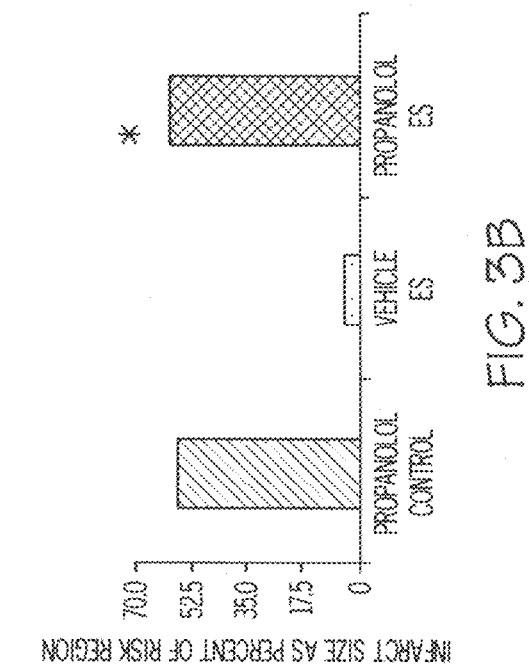
FIG. 3B
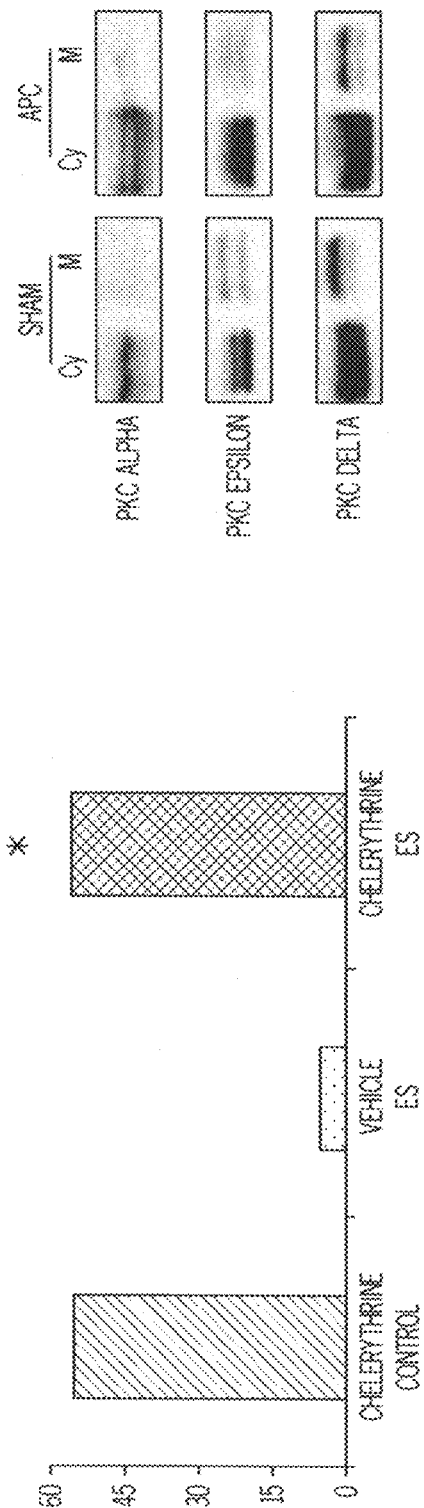
FIG. 3D
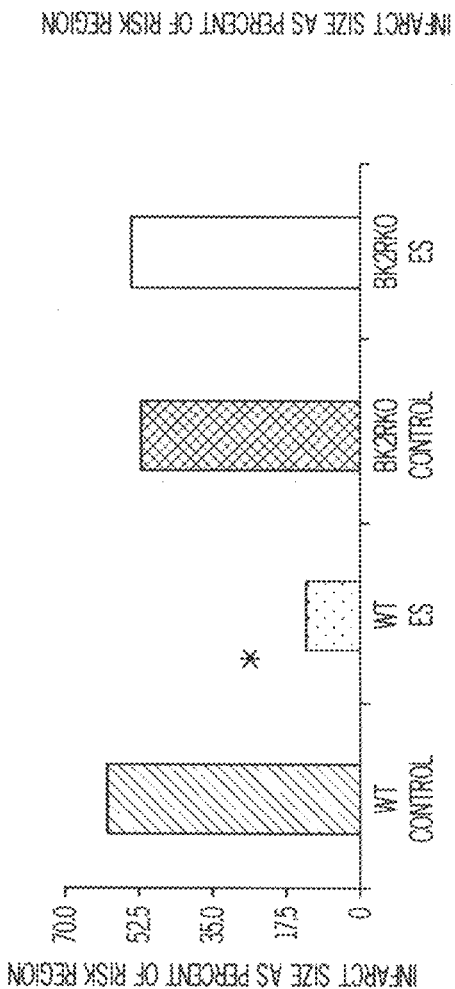
FIG. 3A
FIG. 3C

METHODS OF PREVENTING ISCHEMIC INJURY USING PERIPHERAL NOCICEPTIVE STIMULATION

CROSS-REFERENCE TO RELATED APPLICATIONS

This application claims priority to and benefit of U.S. Provisional Patent Application No. 61/215,616, filed on May 7, 2009 and U.S. Provisional Patent Application No. 61/339,159 filed on Mar. 1, 2010, which are herein incorporated by reference in their entirety.

This application may be related to U.S. patent application Ser. No. 12/800,110, entitled "METHODS OF PREVENTING ISCHEMIC INJURY USING PERIPHERAL NOCICEPTIVE STIMULATION," filed May 7, 2010, by Jones et al., now U.S. Pat. No. 8,980,223, issued Mar. 17, 2015, the entire disclosure of which is incorporated herein by reference in its entirety.

FIELD OF THE INVENTION

This invention relates generally to the activation of TRP as a means of inhibiting ischemia and reperfusion related tissue damage.

BACKGROUND OF THE INVENTION

Ischemia-related injury contributes significantly to morbidity and mortality throughout the world, with perhaps cardiac and cerebral ischemia-related injuries being the most well-known (such as but not limited to heart attack and stroke). Ischemic heart disease is a leading cause of death in North America and is predicted to become more prevalent as the population ages (Scroggins, 2001). Ischemia and reperfusion lead to tissue damage through a variety of mechanisms. For example, ischemia and reperfusion profoundly affect mitochondria and the cytosol. Current therapies for ischemic disease are directed at the restoration of blood flow to the ischemic region. However, during reperfusion additional damage related to generation of reactive oxygen species occurs (Singh et al (1995) *Mol Cell Biochem* 147:77-81 and Flaherty et al (1998) *Free Radic. Biol. Med.* 5:409-419; herein incorporated by reference in their entirety).

The transient receptor potential vanilloid-1 (TRPV1) is a capsaicin responsive ligand-gated cation channel selectively expressed on small, unmyelinated peripheral nerve fibers (cutaneous nociceptors). See Caterina and Julius (2001) *Annu Rev Neurosci* 24:487-517 and Montell et al (2002) *Mol. Cell.* 9:229-231, herein incorporated by reference in their entirety.

Capsaicin, a pungent substance derived from the plants of the solanaceae family (hot chili peppers) has been used as an experimental tool because of its selective action on the small diameter afferent nerve fibers, C-fibers and A-delta fibers that may be involved with signaling pain. Therapeutically capsaicin has been used as a topical analgesic. See for example U.S. Pat. Nos. 4,997,853; 5,063,060; 5,178,879; 5,296,225; 5,665,378; 6,248,788; 6,239,180; and 4,599,342; herein incorporated by reference in their entirety. Capsaicin binds and activates TRPV1.

SUMMARY OF THE INVENTION

Methods and kits for inhibiting ischemia- and/or ischemia/reperfusion-related tissue damage in a subject are provided. The methods and kits are based on the development of means of providing tissue protection, particularly cardiac tissue protection by remote delivery of a TRP agonist to subjects at risk for ischemia-related tissue damage. The methods and kits prevent or reduce ischemia and reperfusion related damage to tissues. Further the application provides methods and kits for cardioprotection in subjects at risk for ischemia-related cardiac tissue damage. Subjects at risk for ischemia-related cardiac tissue damage include, but are not limited to, human subjects with one or more symptoms related to myocardial infarct, or heart attack. The methods and kits provide topical delivery of a therapeutically effective amount of a TRP agonist such as capsaicin to a subject at risk for ischemia-related tissue damage at predetermined regions of the subject's body. Topical administration of the agonist at a predetermined region decreases ischemia-related tissue damage.

Methods and kits for inhibiting ischemia-related tissue damage in a subject are provided. The methods and kits are based on the development of means of providing tissue protection, particularly cardiac tissue protection by remote activation of specific C-fiber nociception by electrical stimulation such as but not limited to electro-acupuncture, to subjects at risk for ischemia-related tissue damage. The methods and kits prevent or reduce ischemia and reperfusion related damage to tissues. Further the application provides methods and kits for cardioprotection in subjects at risk for ischemia-related cardiac tissue damage. Subjects at risk for ischemia-related cardiac tissue damage may include, but are not limited to, human subjects with one or more symptoms related to myocardial infarct, or heart attack. Administration of a therapeutically effective electrical stimulation at a predetermined region decreases ischemia-related tissue damage.

Methods of inhibiting ischemia-related tissue damage in a subject at risk for ischemia-related tissue damage comprising the steps of identifying a subject at risk for ischemia-related tissue damage and topically administering a therapeutically effective amount of a TRPV1 agonist to a predetermined region of said subject are provided. In an embodiment the agonist is selected from the group comprising capsaicin, zucapsaicin, nonivamide, nicoboxil, davasaicin, piperine, rutaecarpine, capsaicinoids, resiniferotoxin, 3-hydroxyacetanilide, anandamide, α-acaridia, β-acaridial, pseudocapsaicin, dihydrocapsaicin, nordihydrocapsaicin anandamide, zingerone, warburganal, polygodial, aframodial, cinnamodial, cinnamosmolide, cinnamolide, isovelleral, scalaradial, ancistrodial, olvanil, merulidial, scutigeral, cannabidiol, civamide, N-arachidonoyldopamine, eugenol, guaiacol, vanillotoxins, and resiniferatoxin (RTX). In an embodiment, the agonist is capsaicin. In an aspect of the invention, the capsaicin consists essentially of trans-capsaicin. In an aspect of the invention, the capsaicin consists essentially of (6E)-N-[(4-Hydroxy-3-methoxyphenyl)methyl]-8-methyl-6-nonenamide. In various aspects, the capsaicin is U.S.P.-grade. In various embodiments the therapeutically effective amount of capsaicin may be within the range of 10 μg to 200 mg capsaicin/kg of said subject. In an aspect of the methods, the therapeutically effective amount of capsaicin is within the range of 1 mg capsaicin/kg subject to 20 mg capsaicin/kg subject. In various embodiments the TRP agonist is administered in the form of an ointment, cream, gel, patch, lotion, or spray.

In an embodiment, the subject is at risk for ischemia-related tissue damage to one or more tissues. In aspects of the methods, the subject is at risk for ischemia-related damage to cardiac, cerebral, renal, intestinal, hepatic, splenic, ocular, retinal, pancreatic, pulmonary, vertebrobasilar or skeletal-muscle tissue. Such a subject is at risk for ischemia-related cardiac, cerebral, renal, splenic, intestinal, hepatic, ocular, retinal, pancreatic, pulmonary; vertebrobasilar or skeletal-muscle tissue damage. In an aspect of the methods, the subject is at risk for ischemia-related cardiac or cerebral tissue damage. In an aspect of the methods, the subject is at risk for ischemia-related cardiac tissue damage. In an aspect of the methods, the predetermined region for administering the agonist in a subject at risk for ischemia-related cardiac tissue damage is selected from the group of regions comprising the region extending from thirty centimeters superior to the umbilicus and to thirty centimeters inferior to the umbilicus and encircling the subject and partial regions within the region extending from thirty centimeters superior to the umbilicus and to thirty centimeters inferior to the umbilicus and encircling the subject. In an aspect of the methods, the predetermined region contains sensory nerves from which signal travels to the dorsal root ganglia at or below the T7 level. In an aspect of the methods, the subject is at risk for conditions that may include, but are not limited to, acute myocardial infarction, angioplasty, cardiac arrest, cardiac surgery, cardiac transplantation or aneurism rupture.

In aspects of the methods the subject is at risk for ischemia-related cerebral tissue damage. Various aspects include methods where the subject is at risk for ischemic stroke, transient ischemic stroke, hemorrhagic stroke, or aneurysm rupture.

Suitable subjects may include mammals, such as but not limited to, human, murine, equine, bovine, caprine, porcine, ovine, canine, or feline mammals. In various aspects the agonist may be administered upon identifying the subject as being at risk for ischemia-related cardiac tissue damage, after identification of an ischemia-related symptom, concomitant with reestablishment of blood flow, or up to three hours after the reestablishment of blood flow. In an aspect, administering the agonist occurs within fifteen minutes of the first identification of an ischemia-related symptom.

The current application provides methods of inhibiting ischemia-related cardiac tissue damage in a human subject comprising the steps of identifying a human subject at risk for ischemia-related cardiac tissue damage and topically administering a therapeutically effective amount of capsaicin to a predetermined region selected from the group of regions comprising the region extending from thirty centimeters superior to the umbilicus to thirty centimeters inferior to the umbilicus and encircling the subject, and one or more partial regions located with the region extending from thirty centimeters superior to the umbilicus to thirty centimeters inferior to the umbilicus and encircling the subject. In an aspect of the methods, administering the capsaicin occurs after identification of an ischemia-related symptom, concomitant with reestablishment of blood flow, or up to three hours after reestablishment of blood flow. In an aspect, administering the capsaicin occurs within fifteen minutes of the first identification of an ischemia-related symptom. Various embodiments may include a therapeutically effective amount of capsaicin within the range of 10 μg to 200 mg capsaicin/kg subject.

An embodiment provides methods of modulating a cardiac tissue damage characteristic comprising the steps of identifying a subject at risk for ischemia-related cardiac tissue damage; topically administering a therapeutically effective amount of a TRPV1 agonist to a predetermined region of the subject and evaluating a cardiac tissue damage characteristic. In an aspect of the embodiment, the TRPV1 agonist is selected from the group comprising capsaicin, zucapsaicin, nonivamide, nicoboxil, davasaicin, piperine, rutaecarpine, capsaicinoids, resiniferotoxin, 3-hydroxyacetanilide, anandamide, α-acaridial, β-acaridial, pseudocapsaicin, dihydrocapsaicin, nordihydrocapsaicin anandamide, zingerone, warburganal, polygodial, aframodial, cinnamodial, cinnamosmolide, cinnamolide, isovelleral, scalaradial, ancistrodial, olvanil, merulidial, scutigeral, cannabidiol, civamide, N-arachidonoyldopamine, eugenol, guaiacol, vanillotoxins, and resiniferatoxin (RTX). In an aspect of the embodiment, the TRPV1 agonist is capsaicin. In an aspect, the therapeutically effective amount of capsaicin is within the range of 10 μg to 200 mg capsaicin/kg of the subject. In an aspect of the methods, administering the capsaicin occurs after identification of an ischemia-related symptom, concomitant with reestablishment of blood flow, or up to three hours after reestablishment of blood flow. In aspects of the methods, the cardiac tissue damage characteristic is a cardiac biomarker selected from the group comprising, but not limited to, troponin and creatine kinase. In aspects of the methods the cardiac tissue damage characteristic is selected from the group comprising cardiac function and cardiac viability.

An embodiment provides methods of modulating the level of at least one cardiac biomarker in the serum of a subject at risk for ischemia-related cardiac tissue damage comprising the steps of identifying a subject at risk for ischemia-related cardiac tissue damage, topically administering a therapeutically effective amount of a TRPV1 agonist to a predetermined region of the subject, obtaining a serum sample from the subject and evaluating the level of at least one cardiac biomarker in the serum wherein the biomarker level is modulated as compared with an untreated or placebo treatment effect. In an aspect of the method, the biomarker level differs from the biomarker level in the serum of an untreated or placebo-treated subject or population of subjects. In an aspect, the cardiac biomarker may include, but is not limited to, troponin or creatine kinase.

An embodiment provides methods of modulating cardiac function in a subject at risk for ischemia-related cardiac tissue damage comprising the steps of identifying a subject at risk for ischemia-related cardiac tissue damage, topically administering a therapeutically effective amount of a TRPV1 agonist to a predetermined region of the subject and performing at least one imaging modality on the subject, wherein the imaging modality indicates the cardiac function is modulated as compared with a similar subject receiving placebo therapy. In aspects of the methods, the imaging modality may include, but is not limited to, echocardiography, nuclear imaging, or magnetic resonance imaging. In aspects of the methods, the cardiac function is improved as compared with a subject receiving placebo therapy.

The current application provides kits for use in preventing ischemia-related damage comprising a TRP family receptor agonist such as, but not limited to, a TRPV1 agonist, in a unit dose form for topical administration and usage instructions. In aspects of the kit, the TRPV1 agonist is selected from the group comprising capsaicin, zucapsaicin, nonivamide, nicoboxil, davasaicin, piperine, rutaecarpine, capsaicinoids, resiniferotoxin, 3-hydroxyacetanilide, anandamide, α-acaridial, β-acaridial, pseudocapsaicin, dihydrocapsaicin, nordihydrocapsaicin anandamide, zingerone, warburganal, polygodial, aframodial, cinnamodial, cinnamosmolide, cinnamolide, isovelleral, scalaradial, ancistrodial, olvanil, merulidial, scutigeral, cannabidiol, civamide, N-arachidonoyldopamine, eugenol, guaiacol, vanillotoxins, and resiniferatoxin (RTX). In an aspect, the agonist is capsaicin. In an aspect of the kit, the kit provides the agonist in the form of an ointment, cream, gel, patch, lotion, liquid, or spray. In an aspect of the kit, the usage instructions provide a predetermined region for administration of the agonist to the subject. In an embodiment of the kit, the kit is for use in preventing ischemia-related cardiac tissue damage. In an aspect of the embodiment wherein the kit is for use in preventing cardiac tissue damage, the predetermined region is a region extending from thirty centimeters superior to the umbilicus to thirty centimeters inferior to the umbilicus and encircling the subject or a partial region within that region.

Methods are provided for inhibiting ischemia-related injury during organ transplantation. The methods comprise topically administering to at least one of the donor and recipient subjects a therapeutically effective amount of a TRPV1 agonist at a predetermined location prior to or concomitant with the organ transplantation procedure.

The application provides methods of inhibiting ischemia-related injury in a mammalian donor organ, comprising topically administering to the donor subject a therapeutically effective amount of a TRPV1 agonist at a predetermined location prior to the organ transplantation procedure.

The application provides methods of inhibiting ischemia-related tissue damage in a subject at risk for ischemia-related damage comprising the steps of: identifying a subject at risk for ischemia-related tissue damage; and topically administering a therapeutically effective amount of a C fiber stimulator. In aspects of the methods, the C fiber stimulator is a TRP family (including but not limited to the TRPV, TRPA, TRPM, TRPP, TRPC subfamilies, each of which has multiple members) receptor agonist, a TRPV1 agonist, capsaicin, capsaicin analogue, or electrical stimulation.

Methods are provided for inhibiting ischemia-related tissue damage in a subject at risk for ischemia-related tissue damage comprising the steps of identifying a subject at risk for ischemia-related tissue damage and topically administering a therapeutically effective electrical stimulation to a predetermined region of the subject. In aspects, the electrical stimulation may include electro-acupuncture. In various aspects, the subject is at risk for ischemia-related tissue damage that may include cardiac, cerebral, renal, pulmonary, intestinal, hepatic, pancreatic, splenic, ocular, retinal, vertebrobasilar, or skeletal-muscular tissue damage. In an aspect, the subject is at risk for ischemia-related cardiac tissue damage. In embodiments wherein the subject is at risk for ischemia-related cardiac tissue damage, the predetermined region may be selected from the group of regions comprising the region extending from thirty centimeters superior to the umbilicus to thirty centimeters inferior to the umbilicus and encircling the subject and at least one partial region located with the region extending from thirty centimeters superior to the umbilicus to thirty centimeters inferior to the umbilicus and encircling the subject. In an aspect of the methods, the predetermined region contains sensory nerves from which signal travels to the dorsal root ganglia at or below the T7 level.

In various embodiments the subject may be at risk for acute myocardial infarction, angioplasty, cardiac arrest, cardiac surgery, cardiac transplantation, or aneurism rupture. In various aspects of the methods, administering the electrical stimulation occurs upon identifying the subject as being at risk for ischemia-related cardiac tissue damage, after identification of an ischemia-related symptom, concomitant with reestablishment of blood flow or up to three hours after reestablishment of blood flow. In aspects of the methods, administering the electrical stimulation occurs within fifteen minutes of the first identification of an ischemia-related symptom.

In an embodiment, methods of modulating an angina related symptom in a subject at risk for angina are provided. The methods involved the steps of identifying a subject at risk for angina and topically administering a therapeutically effective amount of a TRP family receptor agonist to a predetermined region of the subject. In an aspect of the methods, the agonist is administered chronically.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 presents a series of panels describing the murine ischemia/reperfusion model of myocardial infarction and the effects of remote (abdominal) topical nociceptive stimulation on myocardial infarction. These data demonstrate that remote application of either the TRPV1 agonist capsaicin or electrical stimulation of TRPV1 inhibits ischemia-related cardiac tissue damage. Panel A presents images of a murine heart prior to induction of ischemia (A1, pre-ischemia), after surgical induction of ischemia by coronary occlusion (A2, ischemia), and after reestablishment of blood flow (A3, reperfusion) and echocardiographs patterns. Cyanosis was present during ischemia (middle frame, A2). After reperfusion (right frame, A3), cardiac tissue coloration is visibly altered (blushing) compared to cyanotic, ischemic tissue. The hearts were continuously monitored by electrocardiograph (ECG) during the procedure and tracings during each phase are presented beneath the photograph panels (FIG. 1A4 and FIG. 1A5). Voltage (y-axis) is measured in milliVolts; time x-axis) is measured in seconds. During the ischemic portion of the experiment, the ST segment is elevated (A4). Upon reperfusion, the ECG tracing changed from that seen during ischemia (A5). An ECG tracing at 5 minutes after reestablishment of blood flow (reperfusion +5 minutes, A5) is also presented. By 5 minutes post reperfusion, the ECG tracing had changed further. The ECG tracings support this in vivo mouse model of ischemia and reperfusion (I/R).

FIG. 1, panel B presents results obtained from mice were subjected to either remote abdominal electrical stimulation or sham stimulation prior to coronary occlusion. Panels 1B(1) and 1B(2) are triphenyltetrazolium chloride (TTC) stained images of sections of murine hearts taken after 45 minutes of coronary occlusion (CO) and reperfusion showing myocardial infarction. Panel 1B(1) (Nociceptive Stimulus) shows a myocardial infarction in a mouse that received nociceptive stimulation with either abdominal transcutaneous electrical stimulation or chemical stimulation with capsaicin prior to coronary occlusion and induction of ischemia. Panel 1B(2) shows a myocardial infarct from a sham treated mouse (Sham control). Red tissue is living, white tissue is dead, and blue tissue was not in the ischemic region.

FIG. 1, panel C presents a graph summarizing data obtained from mice (n=6) that underwent either electrical stimulation (ES), administration of capsaicin (Capzasin), or sham treatments (Sham) prior to ischemia/reperfusion. Infarct size as a percent of the risk region is presented on the y-axis. Data from sham-treated mice are presented with hatched bars; data from electrically stimulated or capsaicin treated mice are presented with empty bars (nociceptive stimulus). Remote pre-treatment with either capsaicin or electrical stimulation resulted in a substantial reduction in infarct size. In this experiment, remote pre-conditioning (stimulus given 15 minutes prior to the ischemia) reduced the infarct size by 85%. Asterisks indicate P<0.01 compared to the sham values. Values are mean±s.e.m.

FIG. 1, panel D presents a graph summarizing results obtained from sham-treated mice and mice stimulated after induction of ischemia (post-CON). Infarct size as a percent of the risk region is presented on the y-axis. Data from sham-treated mice are presented with hatched bars; data from electrically stimulated mice are presented with cross-hatched bars. Infarct size as a percentage of risk region was significantly reduced in mice that received electrical stimulation during the ischemic period. Further details are provided in example 13. Asterisks indicate P<0.01 compared to the sham values. Values are mean±s.e.m.

FIG. 1, panel E presents photomicrographs of cardiac tissue sections obtained from untreated (normal myocardium, 1E(1)), pre-treated (nociceptive stimulus, 1E(2)) and sham-treated mice (sham control, 1E(3)). The tissue sections were stained with hematoxylin and eosin (H&E staining) prior to imaging. Note the dropout of myocardial cells and infiltration of mononuclear cells, both indicative of ischemia related tissue injury in the sham panel.

FIG. 1, panel F presents photomicrographs of cardiac tissue sections obtained from untreated (normal myocardium, (1F(1)), pre-treated (nociceptive stimulus (1F(2)) and sham-treated mice (sham control (1F(3)). The tissue sections were TUNEL stained prior to imaging. TUNEL positive nuclei fluoresce brightly in this assay and are indicative of programmed cell death (apoptosis). Tissue from sham-treated mice shows significant TUNEL-positive nuclei (bright white regions) while fewer are present in tissue from pre-treated mice. The elevated TUNEL staining in the sham treated cells indicated elevated apoptosis while the reduced level of TUNEL staining in the pre-treated cells indicated a reduced level of apoptosis compared to the sham-treated cells.

FIG. 1, panel G presents a graph summarizing the percentage of apoptotic nuclei in tissue samples from pre-treated and sham-treated mice. FIG. 1, panel H presents a graph summarizing the percentage of DNA fragmentation (also indicative of apoptosis) in tissue samples from pre-treated and sham-treated mice. Data from sham-treated mice are presented with hatched bars; data from electrically stimulated mice are presented with cross-hatched bars (nociceptive). The number of TUNEL positive nuclei and the DNA fragmentation were significantly reduced in the pre-treated group, compared to the sham-treated group (P<0.001, n=4). These data provide evidence that pre-treatment reduces apoptosis and inhibits ischemia-related tissue damage.

Panel B presents a graph of infarct size as a percent of risk region in mice subjected to either spinal cord transection (transection) or sham spinal transection where the spinal cord remained intact (sham). Data from mice where the transection or sham transection was at cervical vertebra 7 (C7) are indicated with empty bars. Data from mice where the transection or sham transection was at thoracic vertebra 7 (T7) are indicated with hatched bars. Immediately after the spinal procedure, mice were subjected to abdominal incision, induction of ischemia and reperfusion. Infarct size was determined 4 hours later. Infarct size as a percentage of the risk region remained significantly high in mice with spinal transection at T7. Asterisks indicate P<0.01 compared to the sham values. Values are mean±s.e.m. Surgical transection at T7 prevents cardioprotection, suggesting that intact spinal nerves to T7 may be required for the stimulus to trigger protection of cardiac tissue. Transection at C7 does not significantly impact cardioprotection suggesting that the central nervous system may have a limited role in cardioprotection through TRP family receptor activation.

Figure 2B:
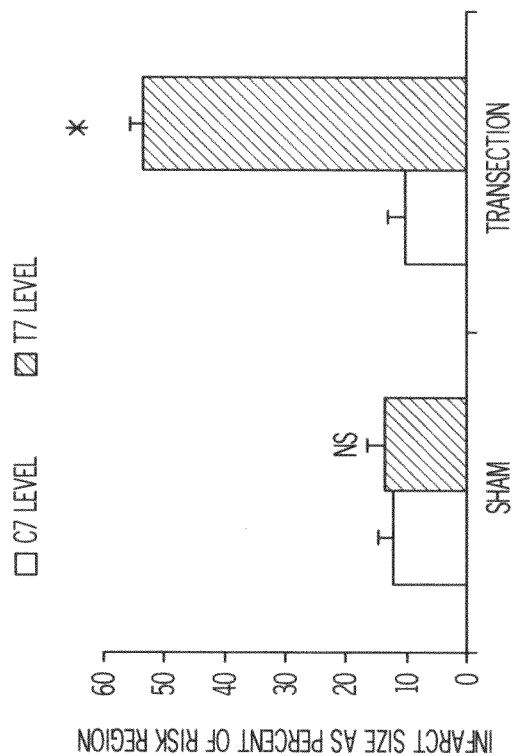
FIG. 2 presents panels summarizing data obtained from experiments evaluating C-fiber neural involvement and consequent molecular signaling in the inhibition of ischemia-related tissue damage. Panel A presents a graph of infarct size as a percent of risk region (y-axis) of sham-treated (no ES, control) or electrically stimulated (ES) mice. The data in the first column (hatched bar) are from control mice that received neither advance treatment nor electrical stimulation prior to induction of ischemia. The data in the middle column (cross-hatched bar) are from mice treated with vehicle prior to electrical stimulation and induction of ischemia (vehicle ES). The data in the last column (dotted bar) are from mice treated with 2% lidocaine prior to electrical stimulation and induction of ischemia (lidocaine ES). Infarction size in lidocaine and ES treated mice shows a significantly higher percentage of risk region than infarction size in vehicle and ES treated mice. Topical lidocaine inhibits nociceptive stimulation of C-fibers and appears to inhibit the cardioprotective effect; thus, nociception of C-fibers at a predetermined location may be involved in eliciting cardioprotection and inhibition of ischemia-related tissue damage.
Figure 2A:
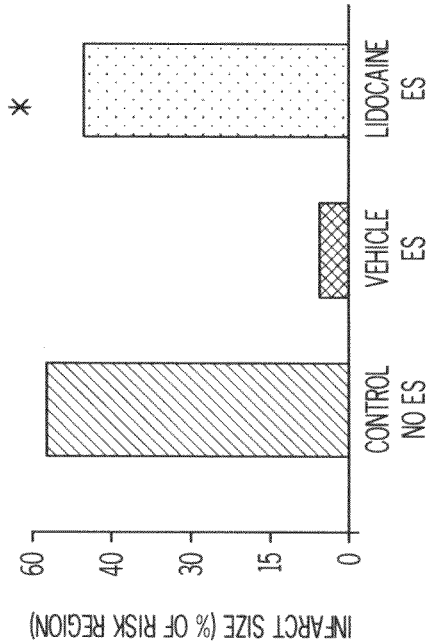

FIG. 2, panel C depicts confocal micrographs of sectioned spinal cord (40 μm) (upper row, 2C(1)-(3)) and whole mount dorsal root ganglia (lower row, (2C(4)-(6)). The formaldehyde fixed spinal cord and dorsal root ganglia at thoracic vertebra T9-T10 (FIG. 2C(3) and FIG. 2C(6) and T1-T5 (FIG. 2C(2) and FIG. 2C(5)) levels were dissected. One week prior to fixation, the mice were injected subcutaneously with a fluorescent dye 1,1'-dioactadecyl-3,3,3',3'-tetramethylindocarbodyanine perchlorate (DiI) at the abdominal incision level (near the level of thoracic vertebra T9-T10 of the spine). After one week, dye labeled sensory neurons and spinal motoneurons at the T9-10 level and neurons at the vertebral T1-T5 level. While not being limited by a mechanism, these data may suggest active neural pathways from the skin sensory nerves to the spine, and from one level of the spine dorsal horn to higher levels, particularly to the T1-5 level, where the cardiac nerves connect to the spinal nerves. This may be a neural pathway from the sensory nerve endings (C-fibers) to the cardiac nervous system. While not being limited by mechanism, the stimulus may activate spinal nerves in the dorsal horn at the level of the incision, these neurons may activate those in the dorsal horn of spinal segments superior, and the signal may travel antidromically along the dorsal root and may activate the sensory fibers innervating the heart (dorsal root reflex).

FIG. 2, panel D presents a graph of results obtained from wild-type (WT) and TRPV1 knock-out (TRPVKO) mice. Infarct size as a percent of risk region is presented on the y-axis. The first bar presents data from wild-type mice subjected to electrical stimulation (WT ES, hatched) prior to surgical induction of ischemia and reperfusion. The second bar presents data from TRPV1 knockout mice subjected to electrical stimulation (TRPVKO ES, dotted) prior to surgical induction of ischemia and reperfusion. The third bar presents data from TRPV1 knockout mice subjected to sham stimulation (TRPVKO no-ES, empty) prior to surgical induction of ischemia and reperfusion. The infarct size as a percent of risk region in TRPV1 knockout mice subjected to electrical stimulation is significantly greater than the infarct size of wild-type mice subjected to electrical stimulation. The reduction of the cardioprotective effect in TRPV1 knockout mice may indicate involvement of TRPV1, a capsaicin sensitive C-fiber cation channel, in inhibition of ischemia-related tissue damage.

FIG. 2, panel E presents a graph of results obtained from wild-type (WT) and TRPV1 knock-out (TRPVKO) mice using topical capsaicin as the cardioprotective stimulus. Infarct size as a percent of risk region is presented on the y-axis. The first bar presents data from wild-type mice topically treated with capsaicin administered to the abdomen prior to surgical induction of ischemia and reperfusion (WT, Capsaicin, hatched bar). The second bar presents data from TRPV1 knockout mice topically treated with capsaicin administered to the abdomen prior to surgical induction of ischemia and reperfusion (TRPVKO, Capsaicin, dotted bar). The third bar presents data from TRPV1 knockout mice subjected to sham treatment prior to surgical induction of ischemia and reperfusion (TRPVKO No capsaicin, empty bar). Wild-type mice treated with capsaicin have reduced myocardial infarct size as compared to TRPVKO mice potentially indicating TRPV1 involvement in inhibition of ischemia-related tissue damage by capsaicin.

The panels of FIG. 3 present data from experiments assessing involvement of additional receptors and mediators in the cardioprotective effect brought about by administration of electrical stimulation or a TRPV1 agonist such as capsaicin. Panel A presents data from wild-type (WT) and bradykinin receptor 2 knockout (BK2RKO) mice subjected to the ischemia/reperfusion protocol described elsewhere herein. Mice were either sham-treated (control, hatched or cross hatched bars) or were electrically stimulated (ES, dotted or empty bars) as described elsewhere herein. Infarct size as a percentage of risk region is presented on the y-axis. Electrical stimulation of wild-type mice significantly reduces the infarct size relative to control wild-type. Electrical stimulation of the bradykinin receptor 2 knockout mice induces no significant reduction of infarct size relative to sham-treated BK2RKO mice. While not limited by mechanism, BK2R may be involved in the inhibition of ischemia-related tissue damage. BK2R is known to be expressed in sympathetic nerve cells and cardiomyocytes.

Panel B presents data from wild-type mice treated with propanolol or vehicle alone. The mice then underwent either sham treatment or electrical stimulation (ES) followed by the ischemia/reperfusion procedure. Propanolol is relatively specific β-adrenergic receptor antagonist. The hatched bar presents data from mice treated with propanolol and subject to sham treatment (propanolol control). The dotted bar presents data from mice treated with vehicle alone and electrically stimulated (vehicle ES). The cross-hatched bar presents data from mice treated with propanolol and electrically stimulated (propanolol ES). Infarct size as a percentage of risk region is presented on the y-axis. Infarct size in mice treated with propanolol and electrically stimulated is significantly higher than infarct size in control mice treated only with the vehicle and electrically stimulated. Blockade of the β-adrenergic receptor reduces development of cardioprotection suggesting involvement of cardiac sympathetic nerves in inhibition of ischemia-related tissue damage.

Panel C presents data from wild-type mice treated with chelerythrine prior to sham treatment or electrical stimulation followed by the ischemia/reperfusion procedure. Chelerythrine is a relatively selective general protein kinase C (PKC) inhibitor. Most previously described forms of preconditioning or postconditioning require PKC activation in cardiomyocytes. Typically this is indicative of activation and/or repression of specific PKC isoforms in the hearts. Infarct size as a percentage of risk region was assessed and is indicated. The hatched bar presents data from mice treated with chelerythrine and subject to sham treatment (chelerythrine control). The dotted bar presents data from mice treated with vehicle alone and electrically stimulated (vehicle ES). The cross-hatched bar presents data from mice treated with chelerythrine and electrically stimulated (chelerythrine ES). In this experiment, inhibition of PKC resulted in reduced inhibition of ischemia-related tissue damage in the chelerythrine and electrically stimulated mice as compared to the vehicle alone and electrically stimulated mice. While not being limited by mechanism, PKC may be involved in the inhibition of ischemia-related tissue damage.

Panel D presents images of Western blotting results on the cytosolic (Cy) and membrane (M) fractions of myocardium. Mice underwent either sham treatment or electrical stimulation. The membranes were incubated with antibodies specific to PKCα, PKCε or PKCδ.

Figure 4:
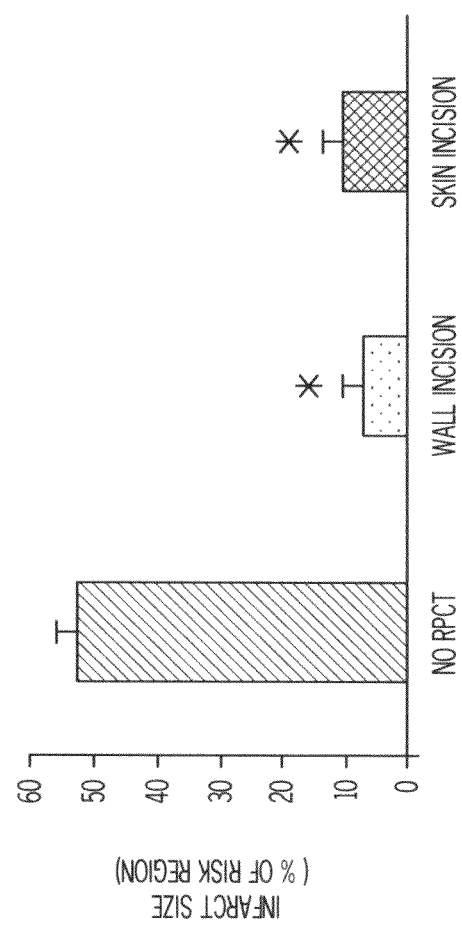

FIG. 4 presents a graph of infarct size as a percentage of risk region in mice subjected to the surgical ischemia and reperfusion protocol described elsewhere herein. Infarct size is on the y-axis. The hatched bar summarizes data from mice that received sham treatment only (No RPCT). The dotted bar summarizes data from mice subjected to an abdominal wall incision prior to ischemia and reperfusion (Wall Incision). The cross-hatched bar summarizes data from mice subjected to an abdominal skin incision prior to ischemia and reperfusion (Skin Incision). Mice pretreated with either an abdominal wall incision or a skin incision exhibited reduced cardiac tissue damage as reflected by the reduced infarct size.

Figure 5:
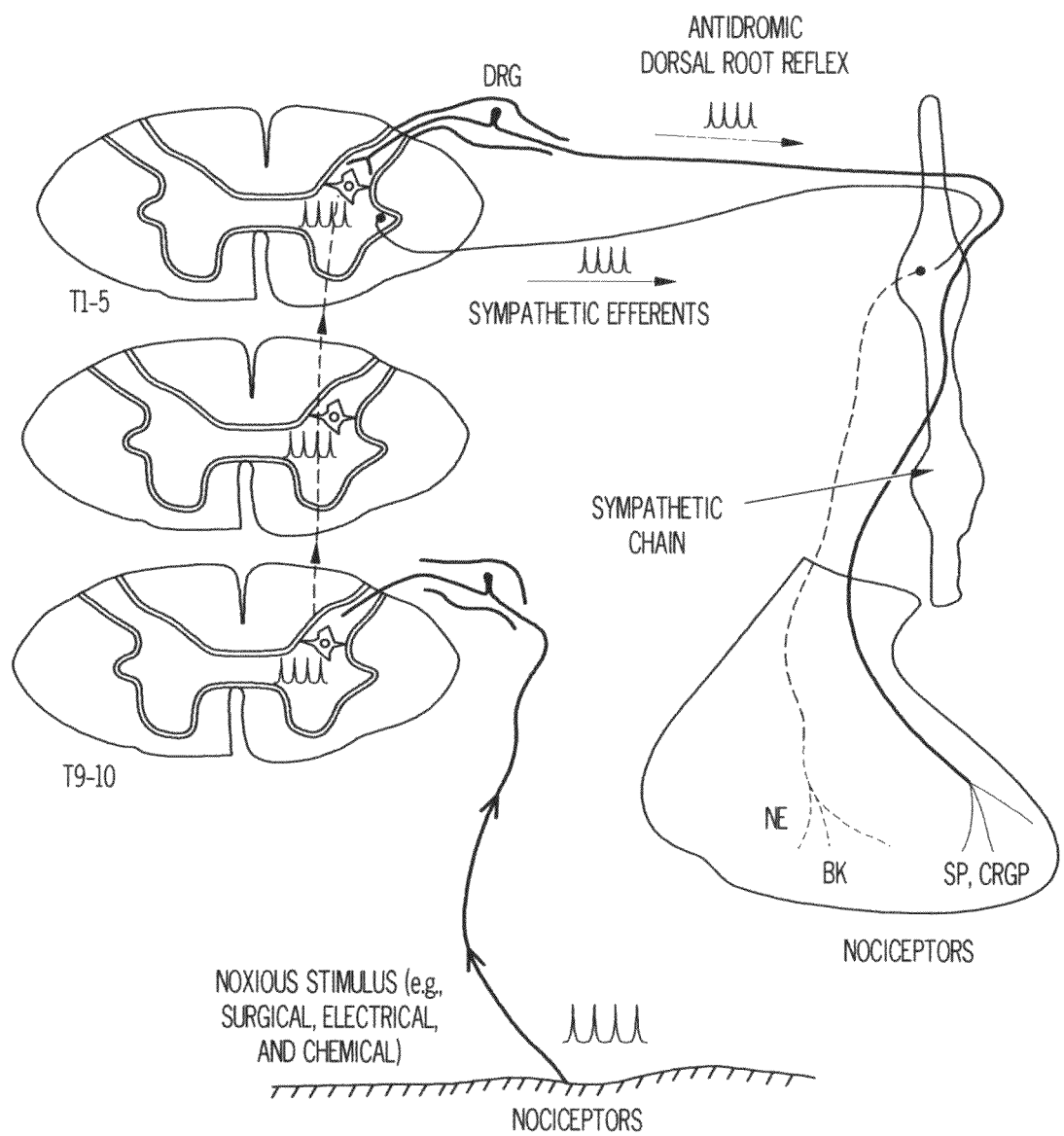

FIG. 5 depicts a cartoon schematic of a possible model of the dorsal root reflex that may be related to the current methods of inhibiting ischemia-related cardiac tissue damage by remotely activating a TRP family receptor. DRG refers to the dorsal root ganglia. BK refers to bradykinin. NE refers to norepinephrine. SP refers to substance P. CRGP refers to calcitonin gene related peptide (CGRP). A nociceptive stimulus by a TRP family receptor agonist, TRPV1 receptor agonist, a TRPV1 agonist, capsaicin, capsaicin analogue, electrical stimulation, incision or other mechanism, may activate a C-fiber sensory nerve, the signal may travel to the dorsal root ganglia at that level and then up the spine perhaps via the dorsal root reflex. At the level of cardiac innervation, the signal may move to the heart, the cardiac sensory nerves may release SP and CGRP and may activate the cardiac sympathetic nerves. The cardiac sympathetic nerves may then release BK and NE which may then bind receptors on the cardiomyocytes.

Figure 6:
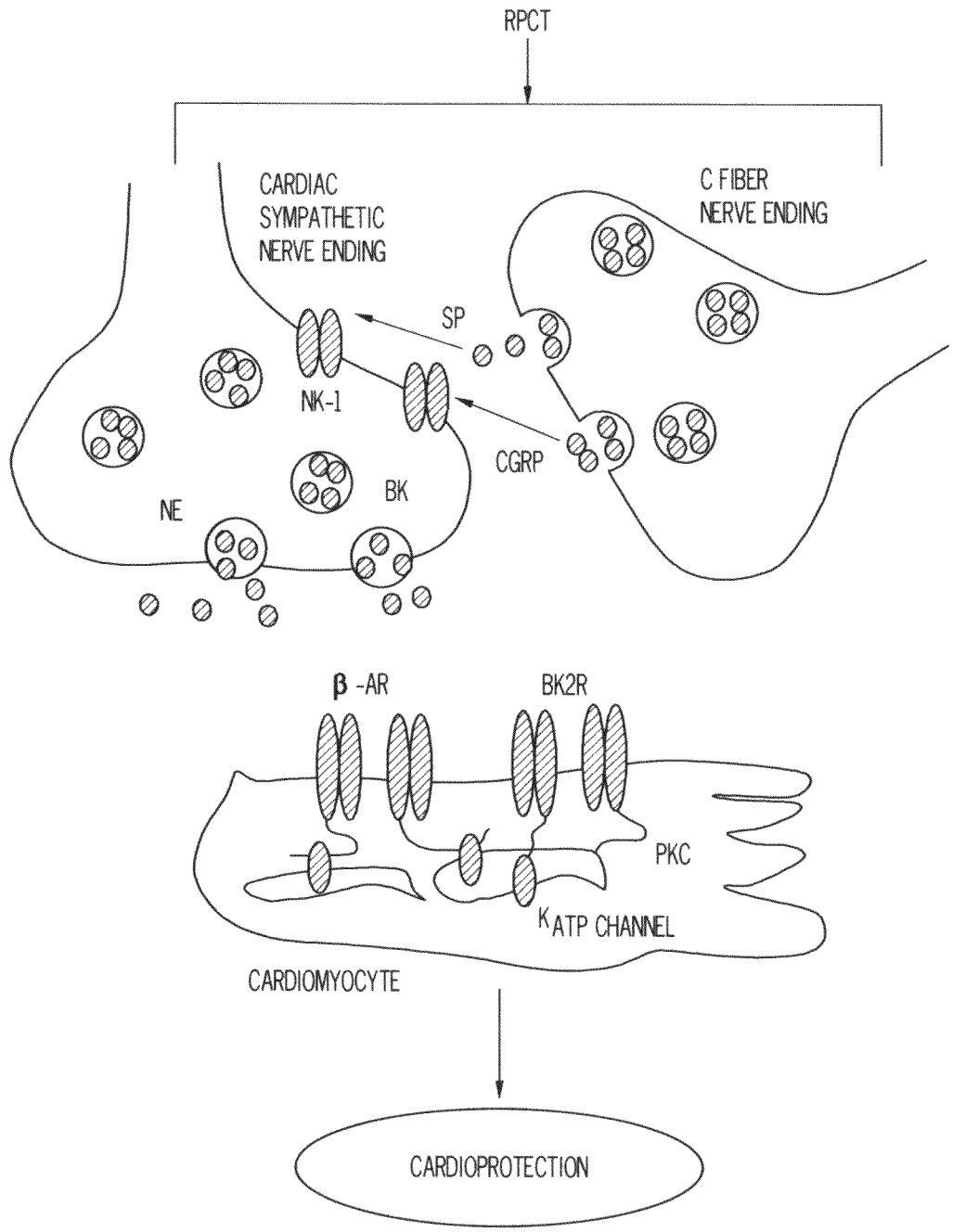
Figure 7A:
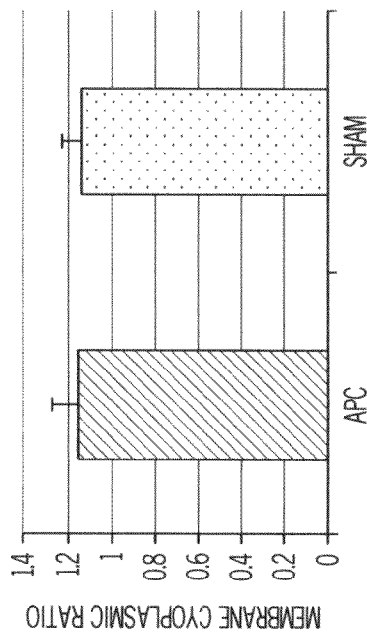
Figure 7B:
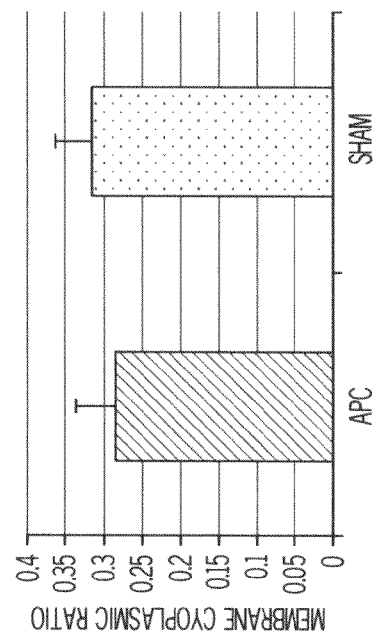
Figure 7C:
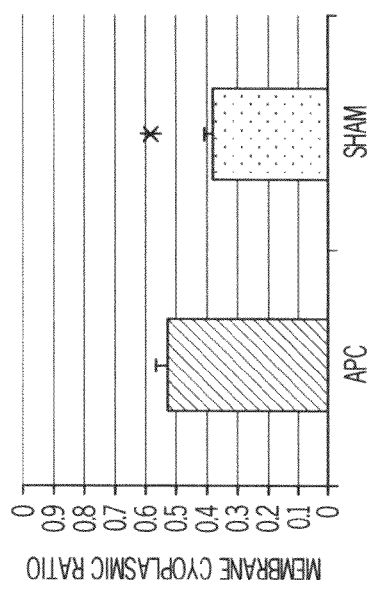
Figure 7D:
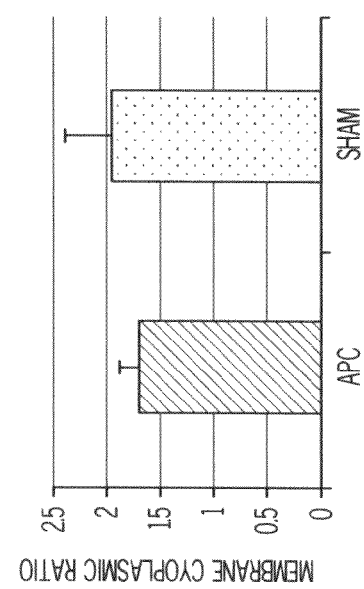

FIG. 6 depicts a possible model of the further aspects of the role of remote C-fiber stimulation in cardioprotection against ischemia/reperfusion related injury. C-fiber stimulation may trigger a nerve impulse in sensory nerves in the heart that may lead to release of neurotransmitters such as CGRP (calcitonin gene related peptide) and substance P. These neurotransmitters may bind receptors activating sympathetic nerves which may then release norepinephrine (NE) and bradykinin (BK). NE may bind to its receptor β-adrenergic receptor (β-AR) and BK may bind to its receptor BK2R, both of which are present on cardiomyocytes. Binding of either or both of these receptors activates or represses specific PKC isoforms and may activate the $K_{ATP}$ channels. The sum result of the modulation of these signaling pathways and effectors may be cardioprotection against ischemia/reperfusion injury.

FIG. 7, panels A-D present quantitative analysis of Western blots using antibodies specific to PKCα (Panel A), PKCε (Panel B), PKCδ (Panel C), and PKCζ (Panel D). The ratio of the cytosolic fraction of the protein to the membrane fraction of the protein is indicated on the y-axis in each graph (Membrane cyoplasmic ratio). Dotted bars indicate results from sham treatment (sham); hatched bars indicate results from electrical treatment (APC). There is an increase in translocation of PKCα and PKCε and a decrease in PKCδ in electrically stimulated cells. This is consistent with the prevailing evidence that PKCε and PKCα may be protective while PKCδ may be injurious.

Figure 8:
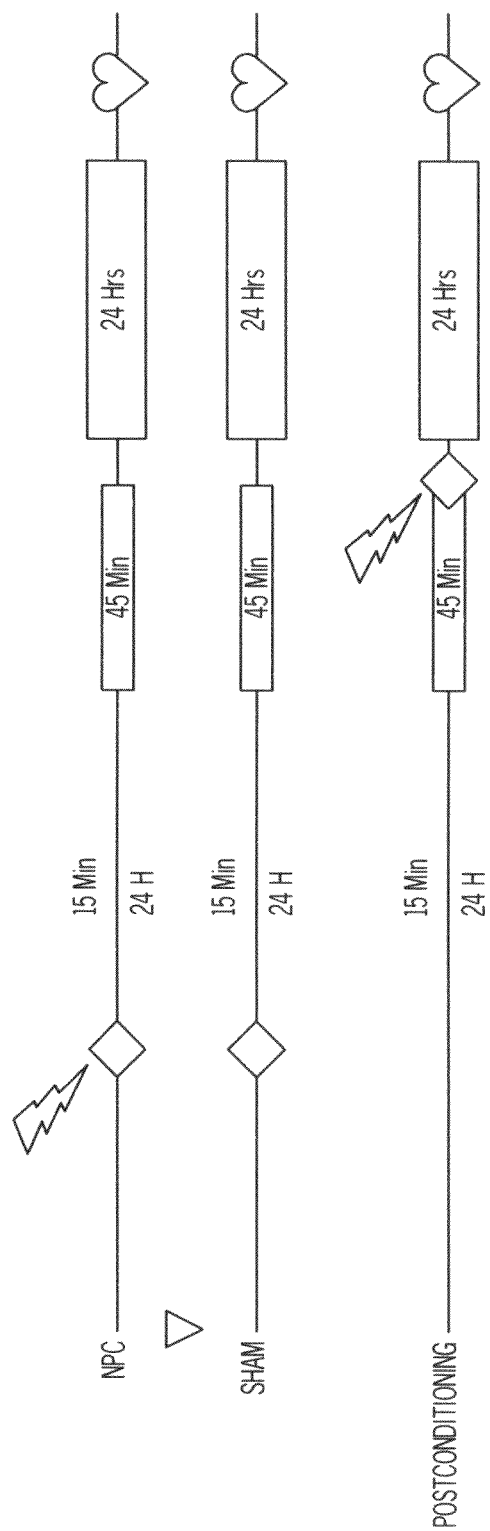

FIG. 8 presents a schematic of pre and postconditioning time lines by way of example.

Figure 9:
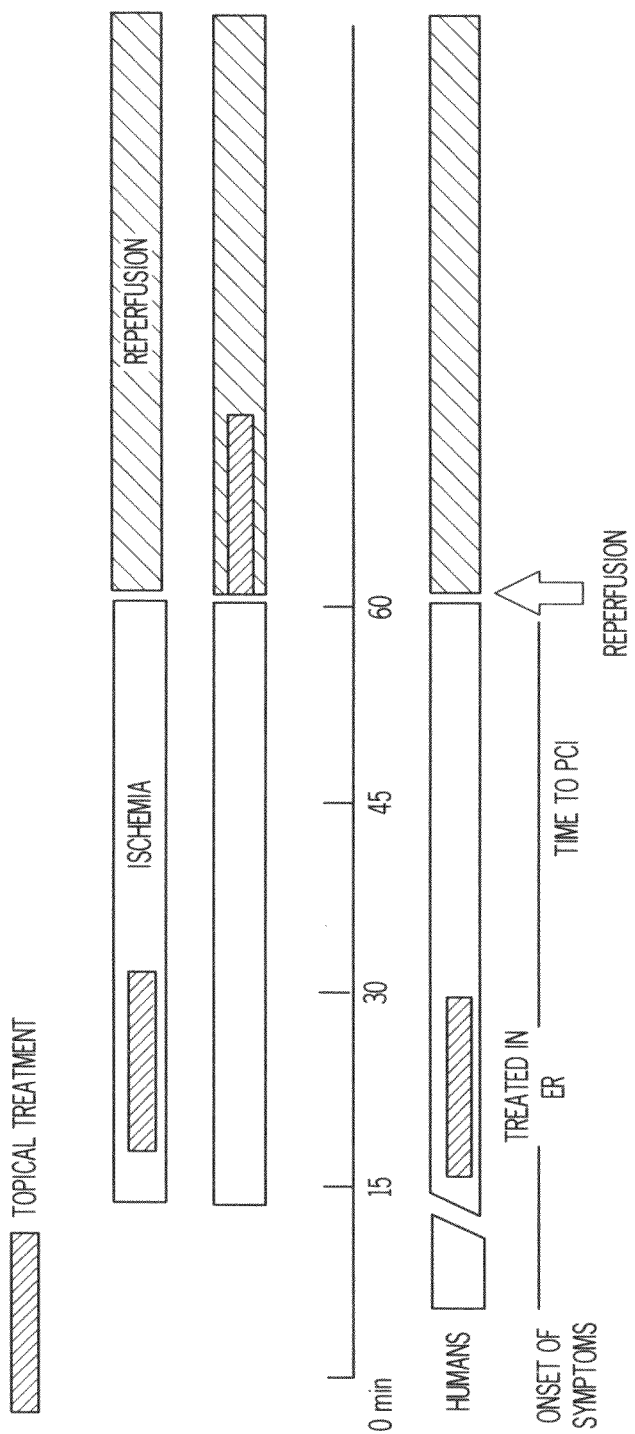

FIG. 9 presents a schematic representation of the course of human ST elevation MI (STEMI) along the bottom and topical administration of a TRPV receptor family agonist in mice in the upper two bars. The timeframe of the topical administration is indicated with a hatched bar. The post-reperfusion time frame is indicated with back-hatched bars (Reperfusion). The diagram indicates the relevance of the mice experiments to human clinical STEMI as compared to postconditioning.

Figure 10:
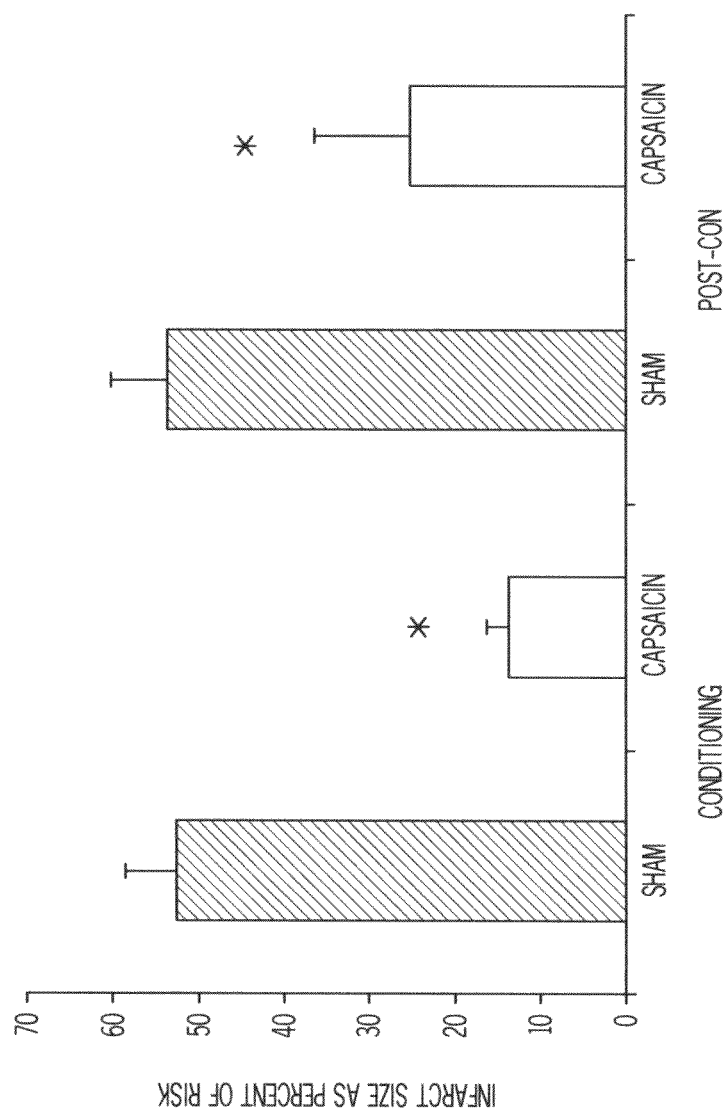

FIG. 10 presents a graph of infarct size as a percent of risk area in mice that received topical capsaicin application (during ischemia=conditioning; after reperfusion=postCON) (empty bars) or sham treatments (hatched bars). Asterisks indicate significant results (p<0.01). Topical capsaicin significantly reduces infarct size.

Figure 11:
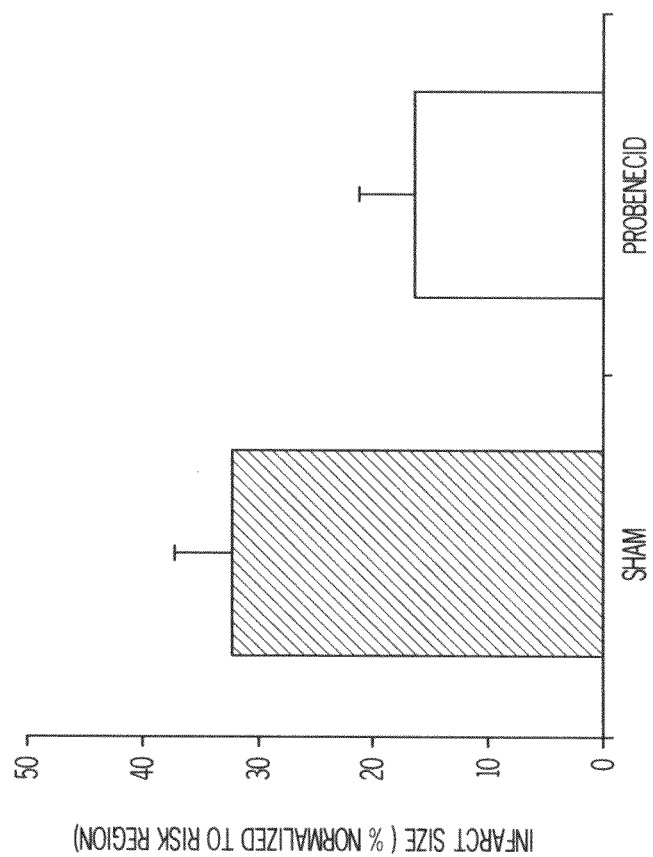

FIG. 11 presents a graph of infarct size as a percent of risk area in mice that received topical probenecid application (empty bars) or sham treatments (hatched bars). Infarct size as a percent of risk region is significantly reduced in mice treated with probenecid, a TRPV2 agonist, compared to control animals (p<0.07).

Figure 12:
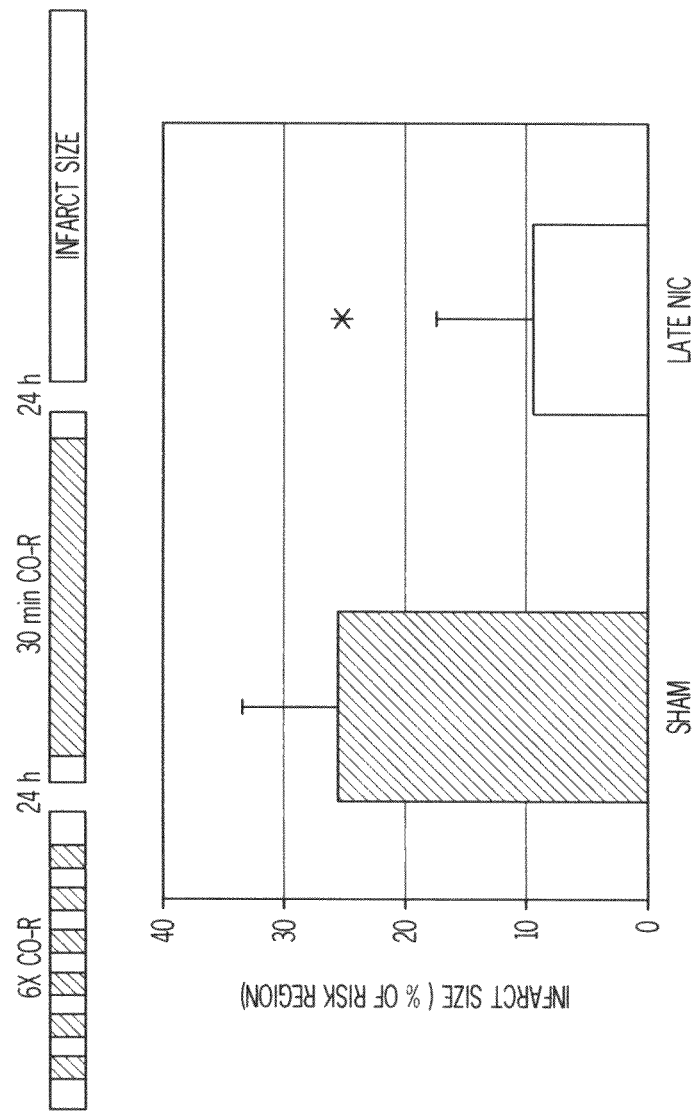

FIG. 12 presents a graph of infarct size as a percent of risk area in mice that received either a sham treatment (sham, hatched bar) or an electrical stimulation (late NIC, empty bar) twenty four hours prior to coronary occlusion/reperfusion. The infarct size as a percent of risk region in mice that received the electrical stimulation was significantly reduced compared to sham treated mice (p≤0.001). The electrical stimulation was applied to the skin in a region below the area corresponding to the T7 vertebral level.

The schematic at the top of the figure represents the timeline of a type of positive control for cardioprotection using multiple, small, non-lethal periods of ischemia (6×CO-R) prior to a 30 minute ischemic period (CO-R) prior to determination of infarct size (infarct size).

DETAILED DESCRIPTION OF THE INVENTION

Remote stimulation of a C fiber provides a protective effect at distant tissues or organs at risk for ischemia-related tissue damage. C fiber stimulation may result from administration of a TRP family receptor agonist, TRPV family receptor agonist, a TRPV1 agonist or electrical stimulation. More particularly, topical administration of a TRPV1 agonist to a predetermined region of a subject inhibits ischemia-related tissue damage. Yet more particularly, topical administration of capsaicin inhibits ischemia-related cardiac tissue damage.

"Inhibiting" means partially or completely blocking, reducing, preventing, lessening, diminishing, or decreasing a particular process or activity. Inhibiting a particular process or activity may be a 0.01%, 0.05%, 0.1%, 0.5%, 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or up to a 100% decrease in the process or activity. Evaluating inhibiting may involve evaluating a result or effect of a particular process or activity.

Ischemia-related tissue damage may include, but is not limited to, cell death, apoptosis, increased inflammation, increased infiltration, mitochondrial damage, acidosis, increased inorganic phosphate, elevated calcium, altered tissue function, altered tissue viability, altered cardiac function, altered cardiac viability, altered cerebral function, altered cerebral viability, and increased long-chain acyl coenzyme A. Methods of evaluating ischemia-related tissue damage may include, but are not limited to, computed tomography (CT), noncontrast CT, magnetic resonance imaging (MRI) scanning, arteriography, and lumbar puncture.

Tissue types that may experience ischemia-related damage may include, but are not limited to, cardiac, cerebral, ocular, retinal, renal, pulmonary, intestinal, hepatic, pancreatic, splenic, vertebrobasilar, and skeletal-muscular tissues. Tissue types of particular interest may include, but are not limited to, cardiac and cerebral tissue.

Suitable subjects may include mammals, such as but not limited to, human, simian, murine, equine, bovine, caprine, porcine, ovine, canine, or feline mammals, mammalian domestic livestock, mammalian companion animals, and mammalian zoo, circus, and research animals.

A subject "at risk for" a particular condition may include subjects exhibiting at least one symptom associated with the condition, subjects exhibiting at least on clinical symptom associated with the condition, subjects in the process of experiencing the condition, and subjects experiencing the condition. A subject at risk for ischemia-related tissue damage may exhibit at least one symptom associated with a condition that results in ischemia, may exhibit at least one clinical symptom associated with a condition that results in ischemia, may be in the process of experiencing a condition that results in ischemia, may exhibit at least one symptom associated with ischemia, may exhibit at least one clinical symptom associated with ischemia, or may be experiencing ischemia. Ischemia-related tissue damage may include tissue damage that results directly from the ischemic incident, tissue damage that results from reperfusion after an ischemic period, and tissue damage that occurs during reperfusion after an ischemic period. Ischemia is a low oxygen state that may result from causes such as but not limited to, obstruction of arterial blood supply or inadequate blood flow leading to hypoxia in the tissue.

Ischemia-related symptoms or symptoms associated with ischemia may include, but are not limited to, sudden severe headache; sudden numbness or weakness of the face, arm or leg, especially on one side of the body; sudden confusion, aphasia, loss of function of extremities, paralysis of extremities; sudden trouble seeing in one or both eyes; sudden dizziness, trouble walking, loss of balance, loss of coordination; facial flaccidness, loss of facial expression, unequal pupil size, tachycardia, coma, incontinence, nausea, convulsions, hypotonia, dysarthria, unresponsive, absence of pulse, cyanosis, dyspnea, cough with sputum, syncope, anxiety, depression, feeling of impending doom, tachycardia, brachycardia; arrhythmia; asystole; ventricular fibrillation, chest pain; pain in arms, neck or jaw; diaphoresis, loss of consciousness, reduced ejection fraction, rales, cold, gallop rhythm, oliguria, anuria, abnormal chest x-ray, dysrrhythmia, altered cardiac enzymes, altered cardiac biomarkers, mixed venous $O_2$, reduced capillary refill, use of accessory muscles, nasal flaring, palpitations, edema, altered vision, light flashes in the visual field, vitreous floaters, loss of sight, blurred vision, loss of visual acuity, hypertension, hypotension, hematuria, elevated BUN/creatinine ratio, and urge to void.

Angina related symptoms may include, but are not limited to, chest discomfort, chest pain, dyspnea, stress-induced ST depression, reversible perfusion abnormality, or wall motion abnormality.

Methods of analyzing, evaluating, assessing or measuring an angina related symptom are known in the art. Such methods may include, but are not limited to exercise tolerance testing (ETT), stress myocardial perfusion imaging, stress echocardiography, ETT with and without Technetium Tc99m Tetrofosmin single photon emission computed tomography (SPECT). Functional classification of angina methods include, but are not limited to, the Canadian Cardiovascular Society Functional Classification of Angina and modifications to include exercise tolerance. See for example Hackett & Cassem (1978) Rehabilitation of the Coronary Patient, John Wiley & Sons p. 243-253 and Shubb et al (1996) Mayo Clinic Practice of Cardiology 3$^{rd}$ Ed. Mosby, p. 1160-1190; herein incorporated by reference in their entirety.

Identifying, noticing, observing, or recognizing a subject that is at risk for a condition may include observing that the subject is experiencing one or more symptoms related to the condition or one or more symptoms related to a disease or disorder related to the condition. Thus, identifying a subject at risk for ischemia-related tissue damage may involve identifying an ischemia-related symptom or identifying a symptom of an ischemia-related condition in the subject. It is envisioned that the methods and kits encompass identification of a symptom of an ischemia-related condition such as heart attack or stroke by the care-provider (such as but not limited to, a first-responder, emergency medical technician, paramedic, layman, clinician) or subject even in instances where the care provider or subject does not fully understand the physiological pathway.

The methods and kits of the invention are useful for the treatment of a variety of diseases, disorders, and conditions that involve ischemia-related tissue damage. Ischemia-related tissue damage may be the basis of a disease, disorder, or condition; may result from a disease, disorder, or condition; or may result from an injury, trauma, tear, or surgical procedure. As used herein, "disease", "disorder", and "condition" may be used interchangeably. Conditions wherein there is a risk of ischemia-related tissue damage to a subject or ischemia-related conditions may include, but are not limited to, reperfusion or revascularization therapy, aneurism rupture, injury and trauma resulting in a significant decrease in blood volume such as but not limited to severing of limbs or digits and replantation thereof, acute myocardial infarction, cardiac infarction, heart attack, cardiac arrest, elective angioplasty, angioplasty, coronary artery bypass graft, cardiac surgery, cardiac bypass, organ transplantation such as cardiac transplantation, head trauma, sepsis, cardiac arrest, drowning, shock, hemorrhage, anaphylaxis, a crush injury, angina, heart failure, cardiovascular collapse, pneumothorax, embolism, decompression sickness, sudden cardiac arrest, SCA, congestive heart failure, myocardial ischemia, coronary artery disease, stroke, cerebral infarction, brain attack, CVA, cerebrovascular accident, transient ischemic attack, transient ischemic stroke, intracranial hemorrhage, cerebral emboli, acute ischemic stroke, hemorrhagic stroke, mini-stroke, ischemic stroke, renal ischemia, ischemic ocular neuropathy, retinal break, retinal detachment, warm ischemia of transplant organs or tissues, stress induced angina, angina pectoris, chronic angina, stable angina, and chest pain.

A subject at risk for ischemia-related cardiac tissue damage may be at risk for a condition such as but not limited to, reperfusion or revascularization therapy, aneurism rupture, injury and trauma resulting in a significant decrease in blood volume such as but not limited to severing of limbs or digits and replantation thereof, acute myocardial infarction, cardiac infarction, heart attack, cardiac arrest, elective angioplasty, angioplasty, coronary artery bypass graft, cardiac surgery, cardiac bypass, organ transplantation such as cardiac transplantation, head trauma, sepsis, cardiac arrest, drowning, shock, hemorrhage, anaphylaxis, a crush injury, angina, heart failure, cardiovascular collapse, pneumothorax, embolism, decompression sickness, sudden cardiac arrest, SCA, congestive heart failure, myocardial ischemia, stress induced angina, angina pectoris, chronic angina, stable angina, chest pain and coronary artery disease.

A subject at risk for ischemia-related cerebral tissue damage may be at risk for a condition such as but not limited to aneurism rupture, stroke, cerebral infarction, brain attack, CVA, cerebrovascular accident, transient ischemic attack, transient ischemic stroke, intracranial hemorrhage, cerebral emboli, acute ischemic stroke, hemorrhagic stroke, mini-stroke, and ischemic stroke.

Methods of modulating angina related symptoms may relieve, ameliorate, improve, alter, change, reduce, or alleviate an angina related symptom. It is recognized that the methods of the instant application may be utilized in conjunction with other methods of modulating an angina related symptom known in the art that may include administering nitrates, beta-blockers, calcium channel antagonists, ranolazine, aspirin, platelet inhibitors, risk factor modification, or surgery.

Methods and kits of the current application provide for topical administration of an agent to a pre-determined region of a subject at risk for ischemia-related tissue damage. A pre-determined region may be an anatomical region of the subject such as a defined, designated, limited, particular or specific area of skin, location of skin, portion of skin, or site. It is recognized that a predetermined region suitable for use with a subject at risk for ischemia-related damage of an indicated tissue may or may not be suitable for use with a subject at risk for ischemia-related damage of a different indicated tissue. Pre-determined regions suitable for use on subjects at risk for ischemia-related cardiac tissue may include, but are not limited to, the upper chest, the arm, the abdomen, the lower abdomen, the upper abdomen, the region extending from thirty centimeters superior to the umbilicus to thirty centimeters inferior to the umbilicus and encircling the subject, and partial regions with in the region extending from thirty centimeters superior to the umbilicus to thirty centimeters inferior to the umbilicus and encircling the subject. Additional suitable regions for use with subjects at risk for ischemia-related cardiac tissue damage may located within a region extending from 60 cm superior to the umbilicus to 50 cm inferior to the umbilicus, 50 cm superior to the umbilicus to 50 cm inferior to the umbilicus, 40 cm superior to the umbilicus to 40 cm inferior to the umbilicus, 45 cm superior to the umbilicus to 45 cm inferior to the umbilicus, 40 cm superior to the umbilicus to 40 cm inferior to the umbilicus, 35 cm superior to the umbilicus to 35 cm inferior to the umbilicus, 30 cm superior to the umbilicus to 30 cm inferior to the umbilicus, 29 cm superior to the umbilicus to 29 cm inferior to the umbilicus, 28 cm superior to the umbilicus to 28 cm inferior to the umbilicus, 27 cm superior to the umbilicus to 27 cm inferior to the umbilicus, 26 cm superior to the umbilicus to 26 cm inferior to the umbilicus, 25 cm superior to the umbilicus to 25 cm inferior to the umbilicus, 24 cm superior to the umbilicus to 24 cm inferior to the umbilicus, 23 cm superior to the umbilicus to 23 cm inferior to the umbilicus, 22 cm superior to the umbilicus to 22 cm inferior to the umbilicus, 21 cm superior to the umbilicus to 21 cm inferior to the umbilicus, 20 cm superior to the umbilicus to 20 cm inferior to the umbilicus, 19 cm superior to the umbilicus to 19 cm inferior to the umbilicus, 18 cm superior to the umbilicus to 18 cm inferior to the umbilicus, 17 cm superior to the umbilicus to 17 cm inferior to the umbilicus, 16 cm superior to the umbilicus to 16 cm inferior to the umbilicus, 15 cm superior to the umbilicus to 15 cm inferior to the umbilicus, 14 cm superior to the umbilicus to 14 cm inferior to the umbilicus, 13 cm superior to the umbilicus to 13 cm inferior to the umbilicus, 12 cm superior to the umbilicus to 12 cm inferior to the umbilicus, 11 cm superior to the umbilicus to 11 cm inferior to the umbilicus, 10 cm superior to the umbilicus to 10 cm inferior to the umbilicus, 9 cm superior to the umbilicus to 9 cm inferior to the umbilicus, 8 cm superior to the umbilicus to 8 cm inferior to the umbilicus, 7 cm superior to the umbilicus to 7 cm inferior to the umbilicus, 6 cm superior to the umbilicus to 6 cm inferior to the umbilicus, 5 cm superior to the umbilicus to 5 cm inferior to the umbilicus, 4 cm superior to the umbilicus to 4 cm inferior to the umbilicus, 3 cm superior to the umbilicus to 3 cm inferior to the umbilicus, 2 cm superior to the umbilicus to 2 cm inferior to the umbilicus, and 1 cm superior to the umbilicus to 1 cm inferior to the umbilicus and encircling the subject, and circular regions radiating up to 30 cm from the umbilicus.

A subject at risk for ischemia-related tissue damage may topically self-administer a TRP family receptor agonist to a predetermined region or the TRP family receptor agonist may be administered by first responders or in an emergency room prior to clinical confirmation of ischemia. A subject at risk for ischemia-related tissue damage may topically self-administer a TRPV1 agonist to a predetermined region or the TRPV1 agonist may be administered by first responders or in an emergency room prior to clinical confirmation of ischemia.

Suitable time frames for topically administering a TRP family receptor agonist or TRPV1 agonist may include, but are not limited to, upon identification that a subject is at risk for ischemia-related tissue damage, after identification of an ischemia-related symptom, concomitant with reestablishment of blood flow, or up to three hours after reestablishment of blood flow. Additional suitable time frames may include but are not limited to within 90, 80, 70, 60, 55, 50, 45, 40, 35, 30, 25, 20, 15, 10, 5 or 1 minute after identification of an ischemia-related symptom and up to 5, 10, 15, 20, 25, 30, 35, 40, 45, 50, 55, 60, 65, 70, 75, 80, 85, 90, 120, 150, or 180 minutes after reestablishment of blood flow. It is recognized that TRP family receptor stimulation may inhibit damage from an ischemia related injury or continue to provide a cardioprotective effect after the stimulation occurs. A late stage cardioprotective effect may occur up to 1, 2, 3, 4, 5, 6, 7, 8, 9, 10, 11, 12, 14, 16, 18, 20, 22, 24, 26, 28, 30, 32, 34, 36, 38, 40, 42, 44, 46, 48, 50, 52 or more hours post TRP family receptor stimulation.

A subject at risk for angina may topically administer a TRP family receptor agonist to a predetermined region or the TRP family receptor agonist may be administered by a medical services provider. A subject at risk for angina may topically self-administer a TRPV1 agonist to a predetermined region or the TRPV1 agonist may be administered by a medical services provider.

Suitable time frames for topically administering a TRP family receptor agonist to a subject at risk for angina may include, but are not limited to chronically or intermittently administering the agonist. By chronically is intended a predetermined dosage schedule such as hourly, daily, weekly, monthly, bimonthly, quarterly, semiannually, annually, biennially, or continuously through a time release or dosage release method, and administration related to an angina symptom inducing factor. It is recognized that continuous administration encompasses replenishment, exchange, replacement, reintroduction, change, and removal and replacement of the agonist delivery system.

Reestablishment of blood flow may occur without intervention or as a result of medical intervention including but not limited to surgical and pharmacological interventions. Any means of reestablishing blood flow known in the art may be used in the methods of the invention. Means of reestablishing blood flow may include, but are not limited to, stent related interventions, coated stent insertions, angioplasty, percutaneous transluminal angioplasty, laser catheterization, atherectomy catheterization, TEC, DVI, angioscopy, radiation catheterization, intravascular ultrasound, rotational atherectomy, radioactive balloons, heatable wires, heatable balloons, biodegradable stent struts, biodegradable sleeves, bypass surgery, angioplasty, blood thinners, tissue plasminogen activator, thrombolytic medications, ultrasound, transcranial Doppler ultrasound, carotid endarterectomy, defibrillation, beta blockers, antiarrhythmic drugs, implantation of a defibrillator, valve replacement surgery, cardiac transplantation, ACE inhibitors, vasodilators, aspirin, clopidogrel, ticlopidine, and streptokinase.

The TRP family may include, but is not limited to, the TRPV, TRPA, TRPM, TRPN, TRPP, TRPVm and TRPC subfamilies. The TRPV family or vanilloid subfamily of heat-sensitive transient receptor potential (TRP) ion channels, may include, but is not limited to TRPV1, TRPV2, TRPV3, and TRPV4. See for example, Gharat & Szallasi (2008) *Expert Opin. Ther. Patents* 18(2):159-209, herein incorporated by reference in its entirety. TRPV1 is also known as capsaicin vanilloid receptor-1 (VR1), capsaicin receptor, type 1 vanilloid receptor, and vanilloid receptor.

A "vanilloid" is capsaicin or any capsaicin analogue that comprises a phenyl ring with two oxygen atoms bound to adjacent ring carbon atoms (one of which carbon atoms is located para to the point of attachment of a third moiety that is bound to the phenyl ring). A vanilloid is a TRPV1 ligand if it binds to TRPV1 with a $K_i$ that is no greater than 10 μM. In various embodiments the $K_i$ is no greater than 10 μM, no greater than 1 μM, no greater than 100 nM, or no greater than 10 nM in a receptor binding assay.

The TRPM and TRPA subfamilies include receptors known as cold receptors. TRPM8 and TRPA1 are cold receptors that may function in protection from ischemia related tissue damage. Cold activation of TRPM8 or TRPA1 may occur through application of a chemical cold patch such as but not limited to patches comprising menthol. Rapid cold producing substances are known in the art.

An agonist means any compound including, but not limited to, small molecules, polypeptides, peptides, agents, and antibodies that activates a receptor.

As used herein a TRP family receptor agonist refers to a compound or agent that elevates an activity of a TRP family receptor above the basal activity level of the receptor. A TRP family receptor agonist activates at least one member of the TRP family of receptors. A TRPV family receptor agonist refers to a compound or agent that elevates an activity of a TRPV family receptor above the basal activity level of the receptor. A TRPV family receptor agonist refers to a compound or agent that elevates an activity of a TRPV family receptor above the basal activity level of the receptor. As used herein a TRPV1 agonist refers to a compound or agent that elevates an activity of TRPV1 above the basal activity level of the receptor. TRPV1 agonists useful in the methods may include a particular compound or agent that may function to elevate an activity of TRPV1 while not affecting another TRPV1 activity. TRPV1 agonists useful in the methods may include selective agonists. A "selective agonist" means that the agonist generally has greater, activity toward a certain receptor(s) compared with other receptors; the selective agonist need not be completely inactive with regards to the other receptors. Methods of assessing activation of TRPV1 may include whole cell patch clamp analysis, ratiometric calcium imaging, excised patch clamp analysis, whole cell tail current analysis, calcium mobilization assay, cultured dorsal root ganglion assay, calcium influx assays, and in vivo pain relief assay. TRPV1 binding assays and competition binding assays may provide additional information about a TRPV1 agonist. See for example 2006/0194805, herein incorporated by reference in its entirety.

TRPV1 activities may include, but are not limited to, triggering C fiber membrane depolarization, opening a cation selective channel, opening a Ca²⁺ ion channel, opening a Na⁺ ion channel, opening a Ca²⁺/Na⁺ ion channel, opening a non-selective ion channel. See for example 2006/0194805, herein incorporated by reference in its entirety.

TRPV1 agonists may include, but are not limited to: capsaicin, piperine, rutaecarpine, capsaicinoids, resiniferatoxin (RTX), N-vanillylnonanamides, N-vanillylsulfonamides, N-vanillylureas, N-vanillylcarbamates, N[(substituted phenyl)methyl]alkylamides, methylene substituted [(substituted phenyl)methyl]alkenamides, N[(substituted phenyl)methyl]-cis-monosaturated alkenamides, N[(substituted phenyl)methyl]diunsaturated amides, 3-hydroxyacetanilide; hydroxyphenylacetamides, pseudocapsaicin, dihydrocapsaicin, nordihydrocapsaicin anandamide, zingerone, warburganal, polygodial, aframodial, cinnamodial, cinnamosmolide, cinnamolide, isovelleral, scalaradial, ancistrodial, β-acaridial, α-acaridial, merulidial, scutigeral, zucapsaicin, nonivamide, nicoboxil, davasaicin, resiniferotoxin, 3-hydroxyacetanilide, anandamide, olvanil, cannabidiol, civamide, eugenol, guaiacol, vanillotoxins, VaTx1, VaTx2, VaTx3, DA-5018, tinyatoxins, spider toxins, arvanil, O-1861, N-arachidonoyl-dopamine (NADA), phenylacetylrinvanil, O-2142, N-oleoyl-dopamine, and oleo-ethanolamide, and capsaicin receptor agonist compounds of Szallasi & Blumberg (1999) *Pharma Reviews* 51:159-211, WO04007495, Gharat & Szallasi (2008) *Expert Opin Ther. Patents* 18(2):159-209, Starowicz et al (2008) *Current Pharmaceutical Design* 14:42-54; and Cromer & McIntyre (2008) *Toxicon* 51:163-173, herein incorporated by reference in their entirety. Additional exemplary TRVP1 agonists are described in U.S. Pat. Nos. 4,599,342; 5,962,532; 5,221,692; 4,313,958; 4,532,139; 4,544,668; 4,564,633; 4,544,669; 4,493,848; 4,544,668; and those described in 20050090557, 20030104085, and 20060194805. Mixtures of agonists and pharmaceutically acceptable salts of any of the foregoing may also be used.

A "pharmaceutically acceptable salt" of a compound recited herein is an acid or base salt that is suitable for use in contact with the tissues of human beings or animals. Such salts include mineral or organic acid salts of basic residues such as amines, as well as alkali or organic salts of acidic residues such as carboxylic acids. Pharmaceutically acceptable salts of compounds are known in the art. See for example, Berge et al (2006) *J. Pharmaceutical Sciences* 66:1-19; Stahl & Wermuth Ed (2008) *Pharmaceutical Salts: Properties, Selection and Use* Verlag; herein incorporated by reference in their entirety.

Capsaicinoids or capsaicin analogues may exhibit similar physiological properties to capsaicin such as for example, trigger C fiber membrane depolarization by opening of cation channels permeable to calcium and sodium. Potency of a capsaicinoid may differ significantly from capsaicin. Capsaicinoids may include, but are not limited to, resiniferatoxin, and compounds described in U.S. Pat. Nos. 5,290,816; 4,812,446; and 4,424,205; WO 96/40079; EPO 149 545; and in Ton et al (1955) *Brit. J. Pharm* 10:175-182; herein incorporated by reference in their entirety. Other capsaicinoids may include, but are not limited to, N-vanillylnonanamides, N-vanillylsulfonamides, N-vanillylureas, N-vanillylcarbamates, N[(substituted phenyl)methyl]alkylamides, methylene substituted [(substituted phenyl)methyl]alkanamides, N[(substituted phenyl)methyl]-cis-monosaturated alkenamides, N[(substituted phenyl)methyl]diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamide, nonivamide, olvanil, N-oleyl-homovanillamidia, isovelleral, scalaradial, ancistrodial, β-acaridial, merulidial, and scutigeral.

TRPV2 agonists may include, but are not limited to, probenecid.

TRPV3 agonists may include, but are not limited to incensole acetate.

TRPV4 agonists may include, but are not limited to, 4 α-phorbol 12,13-didecanoate "Therapeutically effective amount" or "therapeutically effective dose" refers to the quantity or dose of an agent required to produce a clinically desired result such as a biological or chemical response (such as, but not limited to, inhibition of ischemia-related tissue damage in a subject in need of such inhibition), alleviation or amelioration of one or more symptoms of a disease or condition, diminishment of extent of disease, or prevention of damage.

A therapeutically effective amount of capsaicin may be within the range of 10 μg to 10 g capsaicin/kg subject, 10 μg to 5 g capsaicin/kg subject, 10 μg to 3 g capsaicin/kg subject, 10 μg to 2 g capsaicin/kg subject, 10 μg to 1 g capsaicin/kg subject, 10 μg to 500 mg capsaicin/kg subject, 10 μg to 400 mg capsaicin/kg subject, 10 μg to 300 mg capsaicin/kg subject, 10 μg to 200 mg capsaicin/kg (subject), 20 μg to 200 mg capsaicin/kg (subject), 30 μg to 190 mg capsaicin/kg (subject), 40 μg to 180 mg capsaicin/kg subject, 50 μg to 180 mg capsaicin/kg subject, 60 μg to 180 mg capsaicin/kg subject, 70 μg to 180 mg capsaicin/kg subject, 80 μg to 180 mg capsaicin/kg subject, 90 μg to 180 mg capsaicin/kg subject, 0.1 mg to 180 mg capsaicin/kg subject, 0.1 mg to 170 mg capsaicin/kg subject, 0.1 mg to 160 mg capsaicin/kg subject, 0.1 mg to 150 mg capsaicin/kg subject, 0.1 mg to 140 mg capsaicin/kg subject, 0.1 mg to 130 mg capsaicin/kg subject, 0.1 mg to 120 mg capsaicin/kg subject, 0.1 mg to 110 mg capsaicin/kg subject, 0.1 mg to 100 mg capsaicin/kg subject, 0.1 mg to 90 mg capsaicin/kg subject, 0.1 mg to 80 mg capsaicin/kg subject, 0.1 mg to 70 mg capsaicin/kg subject, 0.1 mg to 60 mg capsaicin/kg subject, 0.1 mg to 50 mg capsaicin/kg subject, 0.1 mg to 40 mg capsaicin/kg subject, 0.1 mg to 30 mg capsaicin/kg subject, 0.1 mg to 30 mg capsaicin/kg subject, 0.2 mg to 30 mg capsaicin/kg subject, 0.3 mg to 30 mg capsaicin/kg subject, 0.4 mg to 30 mg capsaicin/kg subject, 0.5 mg to 30 mg capsaicin/kg subject, 0.6 mg to 30 mg capsaicin/kg subject, 0.7 mg to 30 mg capsaicin/kg subject 0.8 mg to 30 mg capsaicin/kg subject, 0.9 mg to 30 mg capsaicin/kg subject, 1 mg to 30 mg capsaicin/kg subject, preferably 1 mg to 20 mg capsaicin/kg (subject), and 9 mg-11 mg capsaicin/kg subject. The concentration of capsaicin in a gel may be within the range of 0.01%-15%, 0.05%-12.5%, 0.05%-10%, 0.1%-10%, 0.1%-9%, 0.1%-8%, 0.1%-7%, 0.1%-6%, 0.1%-5%, 0.1%-4%, 0.1%-3%, 0.1%-2%, or 0.1%-1%.

The capsaicin compounds utilized in the methods and kits provided herein may include, but are not limited to USP-grade capsaicin, trans-capsaicin, (6E)-N-[[(4-Hydroxy-3-methoxyphenyl)methyl]-8-methyl-6-nonenamide and related capsaicinoids.

"Topically administering", "topical", and grammatical equivalents thereof, refer to administering a biologically active compound or electrical stimulation to a pre-defined, pre-determined, definite area, defined, or limited area of the skin. "Topical", "transcutaneous", "transdermal", "transdermic" and "percutaneous" are intended to indicate unbroken skin. Thus, topically administering as used herein does not include administering by subcutaneous injection.

For topical administration, the TRP family receptor agonist including, but not limited to a TRPV agonist, may be formulated by any means known in the art for direct application to a target area such as but not limited to a region extending from thirty centimeters superior to the umbilicus to thirty centimeters inferior to the umbilicus and encircling the subject. Forms chiefly conditioned for topical application may include, but are not limited to, creams, milks, gels, dispersion or microemulsions, lotions, impregnated pads, ointments, or sticks, and aerosol formulations such as, but not limited to, sprays or foams, pastes, jellies and patches. The compositions may be formulated as aqueous compositions or may be formulated as emulsions of one or more oil phases in an aqueous continuous phase. Thus the TRP family receptor agonist may be delivered via patches, bandages, cloths, tissues, swabs, sticks, or brushes. Alternatively the agent may be formulated to be part of an adhesive polymer such as polyacrylate or acrylate/vinyl acetate copolymer.

As described above a TRP family receptor agonist including, but not limited to a TRPV agonist, may be delivered via patches for transdermal administration. See U.S. Pat. No. 5,560,922 for examples of patches suitable for transdermal delivery of a therapeutic agent. Patches for transdermal delivery may comprise a backing layer and a polymer matrix which has dispersed or dissolved therein a therapeutic agent, and may or may not contain one or more skin permeation enhancers. The backing layer can be made of any suitable material which is impermeable to the therapeutic agent. The backing layer serves as a protective cover for the matrix layer and provides also a support function. The backing can be formed so that is essentially the same size layer as the polymer matrix or it can be of larger dimension so that it can extend beyond the side of the polymer matrix and then may extend outwardly in a manner that the surface of the extension of the backing layer may be the base for an adhesive means. Alternatively, the polymer matrix may contain or be formulated with an adhesive polymer such as polyacrylate or acrylate/vinyl acetate copolymer.

Examples of materials suitable for making the backing layer may include, but are not limited to, films of high and low density polyethylene, polypropylene, polyurethane, polyvinylchloride, polyesters such as poly(ethylene phthalate), metal foils, metal foil laminates of such suitable polymer films and the like. Preferably the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness may be from about 10 to about 200 microns. In an embodiment, a patch for transdermal delivery of a TRP family receptor agonist may be provided with a placement guide. A placement guide facilitates administration at the appropriate pre-determined site. A placement guide may be structural, pictorial, verbal or a combination thereof. The placement guide may be integral to the patch, removable from the patch or separate from the patch.

Generally those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, cross-linked polymers (hydrogel), polyvinylidene chloride, poly(ethylene terephthalate), butyl rubber, epichlorohydrin rubbers, ethylenvinyl alcohol copolymers, for example, polysiloxane-polycarbonate copolymers, polysiloxane-poly-ethylene oxide copolymers, polysiloxane-polymethacrylate copolymers, polysiloxane-alkylene copolymers (e.g. polysiloxane-ethylene copolymers), polysiloxane-alkylenesilane copolymers (e.g. polysiloxane-ethylenesilane copolymers), and the like; cellulose polymers for example methyl or ethyl cellulose; hydroxylpropyl methyl cellulose, and cellulose esters; polycarbonates, polytetrafluoroethylene, and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimmethacrylate, trimethylol propane trimethacrylate and the like. Other monomers which provide such sites include allyl acrylate, allyl methacrylate, diallyl maleate and the like.

A plasticizer and/or humectant may be dispersed within the adhesive polymer matrix. Water-soluble polyols may be suitable for this purpose. Incorporation of a humectant in the formulation allows the dosage unit to absorb moisture on the surface of the skin which in turn helps to reduce skin irritation and to prevent the adhesive polymer layer of the delivery system from failing.

Ointments and creams may, for example, be formulated with an aqueous or oily base with the addition of suitable thickening and/or gelling agents. Lotions may be formulated with an aqueous or oily base and may contain one or more emulsifying agents, stabilizing agents, dispersing agents, suspending agents, thickening agents, or coloring agents. The percent by weight of a therapeutic agent of the invention present in a topical formulation may depend on various factors, but generally may be from about 0.01% to 95% of the total weight of the formulation, and typically 0.1 to 85% of the total weight of the formulation.

In various embodiments the TRP family receptor agonist including, but not limited to a TRPV agonist, may be topically administered using a sponge, aerosol, spray, brush, swab, or other applicator. The applicator may provide either a fixed or variable metered dose application such as a metered dose aerosol, a stored-energy metered dose pump, or manual metered dose pump. The applicator may have measuring marks for assisting a user in determining the amount of the composition in the applicator device.

Modulating may be altering, changing, varying, affecting, adjusting, or regulating something of interest, such as ischemia-related tissue damage, tissue damage, or a cardiac tissue damage characteristic. Modulating may encompass improving a cardiac tissue damage characteristic or increasing or decreasing a cardiac tissue damage characteristic by at least 1%, 5%, preferably 10%, 20%, more preferably 30%, 40%, 50%, 60%, yet more preferably 70%, 80%, 90%, or 100% as compared to an untreated or placebo treatment effect. "Improving a cardiac tissue damage characteristic" means changing, altering, moving, shifting or returning a tissue damage characteristic to a state or level closer to that found in a subject not undergoing an ischemia-related event such as a healthy or normal subject. Any method of evaluating a tissue damage characteristic known in the art may be used in the provided methods. It is recognized that the effects of the methods provided herein may be compared to an untreated or placebo effect in an individual or population prior to the use of the methods or kits.

Cardiac tissue damage characteristics may include, but are not limited to, altered cardiac function, altered ECG patterns, arrhythmias, dysrrhythmias, left ventricular (LV) function, LV systolic function parameters such as but not limited to, left ventricular dimension, stroke volume index, LV fractional shortening, LV ejection fraction, or peak systolic strain; diastolic and systolic dimensions, intraventricular septum thickness, LV posterior wall thickness, left atrial dimension, ejection fraction and altered cardiac biomarkers.

Methods of evaluating cardiac function or cardiac viability may include, but are not limited to, serial echocardiogram, two dimensional speckle tracking imaging, transthoracic echocardiogram, echo-Doppler, electrocardiogram (ECG), serial ECG, continuous ECG, stress testing, electrophysiological testing, tilt table testing, radiological procedures, x-rays, ultrasonography, M-mode ultrasound, two-dimensional ultrasound, Doppler ultrasound, color Doppler, echocardiography, MRI, magnetic resonance angiography (MRA), radionuclide imaging, positron emission tomography (PET), cardiac catheterization, central venous catheterization, angiography, cineangiography, computed tomography (CT), computed tomography angiography (CTA), fluoroscopy, hematoxylin & eosin staining, annexin staining, and TUNEL staining.

Cardiac biomarkers may include, but are not limited to troponin, serum creatine kinase, plasma CGRP, blood urea nitrogen, serum creatinine, serum potassium, serum sodium, serum chloride, serum bicarbonate, troponin T, troponin I, CK-MB, myoglobin, and NT-proBNP. Any method of evaluating a cardiac biomarker known in the art may be used in the methods of the invention.

Any method of performing an imaging modality known in the art may be utilized in the methods and kits provided herein. Imaging modalities may include, but are not limited to, serial echocardiogram, two dimensional speckle tracking imaging, transthoracic echocardiogram, echo-Doppler, electrocardiogram (ECG), serial ECG, continuous ECG, x-rays, ultrasonography, M-mode ultrasound, two-dimensional ultrasound, Doppler ultrasound, color Doppler, echocardiography, MRI, magnetic resonance angiography (MRA), radionuclide imaging, positron emission tomography (PET), cardiac catheterization, central venous catheterization, angiography, cineangiography, computed tomography (CT), computed tomography angiography (CTA), and fluoroscopy.

"Biological sample" means a sample collected from a subject including, but not limited to, whole blood, serum, tissue, cells, mucosa, fluid, scrapings, hairs, cell lysates, urine, and secretions. Biological samples such as serum samples can be obtained by any method known to one skilled in the art. Further, biological samples can be enriched, purified, isolated, or stabilized by any method known to one skilled in the art. Such enrichment, purification, isolation, or stabilization procedures can be performed at any time during the methods of the invention. A person skilled in the art of obtaining biological samples would recognize various benefits and drawbacks associated with the different methodologies and would choose accordingly.

Kits provided herein may comprise a TRP family receptor agonist such as but not limited to, a TRPV agonist, in one or more dosage unit forms for use in the methods and usage instructions. Preferredly the usage instructions will indicate the appropriate predetermined location for topical administration of the TRPV1 agonist for the type of tissue damage that the subject is at risk for. It is envisioned that the dosage unit form may be optimized for the predetermined location appropriate for a particular condition or indication.

"Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Organ transplantation may include, but is not limited to, removal of an organ, portion of an organ, or tissue from a donor subject and re-implantation of the organ or portion of an organ in a recipient subject. A donor subject is a subject from which the organ, portion of an organ, or tissue is removed. The donor subject may be a living subject (as for example with a kidney transplant) or a dead subject. A recipient subject is a subject in which the organ, portion of an organ, or tissue is implanted, grafted, or placed. In an embodiment, the donor subject and the recipient subject may be the same individual, as for instance, with a muscle or skin graft. The methods encompass administering a TRP family receptor agonist such as, but not limited to a TRPV1 agonist, to at least one of the donor and recipient subjects prior to or concomitant with the organ transplantation procedure. The organ transplantation procedure has multiple components and it is recognized that the time frames suitable for administering a a TRP family receptor agonist such as, but not limited to a TRPV1 agonist to a donor subject may differ from those suitable for a recipient subject. Components of the organ transplantation procedure may include, but are not limited to, preparation of the donor subject, removal of the desired organ, organ portion, or tissue from the donor, transportation of the donated organ, organ portion, or tissue to the recipient, preparation of the recipient subject, and implantation, grafting, or connecting of the donated organ, organ portion or tissue.

Methods and kits provided herein may include methods and kits for ischemia-related tissue damage in a subject at risk for ischemia-related tissue damage comprising the steps of identifying a subject at risk for ischemia-related tissue damage and topically administering a therapeutically effective amount of a C-fiber stimulator. C-fiber stimulators may include, but are not limited to, TRP family receptor agonists, TRPV family receptor agonists, TRPV1 agonists, capsaicin, capsaicin analogues and electrical stimulation. C-fibers, C sensory fibers, and C fiber nociceptors may be used interchangeably herein and refer to a type of peripheral pain carrying nerve fiber. C-fibers include both TRPV1 positive C-fibers and TRPV1 negative C-fibers. TRP family pain receptor channels including, but not limited to the TRPV1 pain receptor channel, are activated by transdermal electrical stimulation. Transdermal electrical stimulation may activate one or more TRP family pain receptor channels. Electrical stimulation that may be utilized in the provided methods may include, but is not limited to, transcutaneous electrical stimulation and electroacupuncture. Therapeutically effective electrical stimulation may include up to 1, 5, 10, 15, 20, 25, 30, 35, 40, 45, 50, 55, or 60 minutes of pulsing transcutaneous electrical stimulation. Such pulsing may be within the range of 1-30 volts, 2-20 volts, 3-19 volts, 4-18 volts, 5-17 volts, 6-16 volts, 7-15 volts, 8-14 volts, 8-12 volts, and 9-11 volts. The duration of the pulse may range from 0.1-2 ms, 0.1-1.5 ms, 0.1-1 ms, 0.1-0.9 ms, 0.1-0.8 ms, 0.1-0.7 ms, 0.2-0.6 ms, 0.3-0.6 ms, and 0.4-0.6 ms. The frequency may range from 1-500 Hz, 10-400 Hz, 20-300 Hz, 30-200 Hz, 40-170 Hz, 50-140 Hz, 60-130 Hz, 70-120 Hz, 80-110 Hz, and 90-105 Hz.

The following examples are offered by way of illustration and not limitation.

EXPERIMENTAL

Example 1

Mice

Wild-type (B6129SF2/J F2) and bradykinin 2 receptor knockout (BK2R KO) mice (B6129 SF2/J F2, strain 101045) were obtained from Jackson Laboratories (Bar Harbor, Me.). Mice were maintained in accordance with institutional guidelines, the Guide for the Care and Use of Laboratory Animals (NIH, revised 1985) and the Position of the American Heart Association on Research Animal Use (1984). All groups of mice consisted of males and females distributed equally among groups; post-hoc analysis confirmed previous results that there were no gender related differences in these studies.

Example 2

Mouse Model of Ischemia and Reperfusion

A previously described mouse model of ischemia and reperfusion (I/R) injury in vivo was used (Ren et al. (2004) *J. Surg. Res.* 121(1):120-129; Fan et al (2005) *Circulation* 111 (14):1792-1799; Zhou et al (2007) *Cardiovascular Research* 75(3) 487-497; and Diwan et al (2007) *J. Clinical Investigation* 117(10):2825-2833, herein incorporated by reference in their entirety). Mice were anesthetized with sodium pentobarbital (90 mg/kg ip), intubated with PE 90 tubing and ventilated using a mouse miniventilator (Harvard Apparatus, Holliston, Mass.). All mice were continuously monitored by electrocardiography (ECG) (DigiMed Sinus Rhythm Analyzer, Micro-Med Inc), and mice without evidence of ischemia and timely reperfusion were excluded from the studies.

A lateral thoracotomy (1.5 cm incision between the second and third ribs was performed to provide exposure of the left anterior descending coronary artery (LAD). Vascular bundles in the vicinity were coagulated using a microcoagulator (Medical Industries Inc, St. Petersburg Fla.). An 8-0 nylon suture was placed around the LAD 2-3 mm from the tip of the left auricle and a piece of soft silicon tubing (0.64 mm ID, 1.19 mm OD) was placed over the artery. Coronary occlusion was achieved by tightening and tying the suture. Coronary occlusion was for 45 minutes, unless indicated otherwise. At the end of the occlusion, the suture was untied and left in place. Ischemia was confirmed by visual observation of cyanosis and by continuous ECG monitoring (QRS complex widening, T wave inversion and ST segment changes); reperfusion was confirmed by reversal of these effects. Results of one such experiment are presented in FIG. 1, panel A.

Example 3

Infarct Size Determination and Imaging

Mice were euthanized either 4 or 24 hours after reperfusion and infarct size determination and imaging were performed by previously described methods (Ren et al. (2004) *J. Surg. Res.* 121(1):120-129 and Guo et al (1998) *Am J. Physiology* 275 (4 Pt 2):H1375-1387, herein incorporated by reference in their entirety). Mice were anesthetized with pentobarbital sodium (35 mg/kg iv) and euthanized with an intravenous bolus of KCl. The heart was excised and perfused with Krebs-Henseleit solution through an aortic cannula (22 or 23-gauge needle) using a Langerdorff apparatus. To delineate infarcted from viable myocardium, the heart was then perfused with a 1% solution of 2,3,5-triphenyltetrazolium chloride (TTC) in phosphate buffer (pH 7.4, 37° C.) at a pressure of 60 mM Hg (approx. 3 ml over 3 min). To delineate the occluded-reperfused coronary vascular bed, the coronary artery was then tied at the site of the previous occlusion and the aortic root was perfused with a 5% solution of phthalo blue dye in normal saline. The portion of the left ventricle (LV) supplied by the previously occluded coronary artery (risk region) was identified by the absence of blue dye, whereas the rest of the LV was stained dark blue. The heart was frozen. Atrial and right ventricular tissues were excised. The LV was sectioned into 5-7 transverse slices which were fixed in 10% neutral buffered formaldehyde. The sections were photographed using a Nikon Coolpix880 digital camera fitted with UR-E2 macro lens and computerized digital planimetry was performed using NIH Image software. Infarct size was determined by the method of Fishbein et al (1981) *Am Heart J* 101(5):593-600, herein incorporated by reference in its entirety. The four hour time point was used only in the spinal transection and related control studies.

Example 4

Abdominal and Skin Incisions

Two cm abdominal incisions were made through the skin, subcutaneous, fat, muscle, and peritoneum at the abdominal midline. For skin incisions, the incision was made anatomically in the same location but care was taken to cut the skin only. Control mice were intubated, shaved, and the skin was sterilized but no incision was made.

Example 5

Spinal Cord Transection

Spinal cord transection was used to investigate the involvement of the central nervous system in the cardioprotective effect of TRPV1 activation. Mice were anesthetized and bone markers were identified at C7 and T7 vertebra levels. The spinal cords of cervical 7 (C7) and thoracic 7 (T7) were transected by a sharp knife with limited bleeding under a microscope followed by immediate abdominal incision. Fifteen minutes later, the mice were subjected to the surgical ischemia/reperfusion protocol described above herein. Fours hours after reperfusion, mice were euthanized and infarct size determination was performed without the mice regaining consciousness. Results from one such experiment are presented in FIG. 2, panel B.

Example 6

Neuronal Tracing

A fluorescent dye 1,1'-dioactadecyl-3,3,3',3'-tetramethylindocarbodyanine perchlorate (DiI) was injected subcutaneously at the abdominal incision level (thoracic vertebra T9-T10) of the spine. One week after injection, mice were perfused with 4% formaldehyde. The fixed spinal cord and dorsal root ganglia at thoracic vertebra T9-T10 and T1-T5 levels were dissected. The sectioned spinal cord (40 µm) and whole mount dorsal root ganglion were visualized by confocal microscopy. Images captured from one such experiment are shown in FIG. 2, panel C.

Example 7

Morphological and Histological Assessment of Cardiac Tissue

Hematoxylin and eosin staining were performed to evaluate cardiac tissue after exposure to surgically induced ischemia and reperfusion. Mice were euthanized 24 hours after surgery. Hearts were perfused with PBS then fixed by perfusion with 10% formalin in PBS. Hearts were post-fixed overnight, embedded in paraffin, sectioned, stained, and examined microscopically. Results from one such experiment are presented in FIG. 1, E.

Example 8

Evaluation of Apoptosis

Mice were euthanized 24 hours after surgery. Hearts were perfused with PBS then fixed by perfusion with 10% formalin in PBS. Hearts were post-fixed overnight, embedded in paraffin and sectioned. In situ DNA fragmentation was assessed using the DeadEnd™ Fluorometric TUNEL system (Promega), followed by staining with anti-sarcomeric actin antibody (Sigma) and DAPI (Invitrogen). TUNEL-positive (green) nuclei were counted from 10 randomly chosen microscopic fields of the midventricular section (n=5) and were expressed as a percentage of total nuclei (both blue and green staining nuclei; approximately 400 nuclei counted per field) in the same fields. Results from one such experiment are presented in FIG. 1.

Example 9

Evaluation of Apoptosis (2)

DNA fragmentation in cardiac tissue post-ischemia/reperfusion was assessed by a cell-death detection ELISA kit (Roche Applied Science). The cell-death detection ELISA measures the content of cytosolic mono- and oligo-nucleosomes (180 base pair nucleotides or multiples) by employing the sandwich enzyme immunoassay technique. Results were normalized to the standard provided in the kit and expressed as a fold-increase over the control.

Example 10

Remote Capsaicin Inhibition of Ischemia-Related Tissue Damage (1)

Gender matched mice were obtained. Experimental and sham (control) treated mice were shaved and prepped similarly. Capsaicin gel (0.1% capsaicin in a gel carrier, 200-250 µl) was applied to a 25 g mouse. This is approximately 10 mg/kg body weight. Fifteen minutes later ischemia and reperfusion were surgically induced as described elsewhere herein. The coronary occlusion was maintained for 45 minutes and then released, allowing reperfusion and reestablishing blood flow. Infarct size was determined as described elsewhere herein.

Example 11

Remote Capsaicin Inhibition of Ischemia-Related Tissue Damage (2)

Gender matched mice were obtained. Experimental and control treated mice were shaved and prepped similarly (n=6 mice per group). Capsaicin (0.1% capzacin cream) was administered over a 2 $cm^2$ skin area at the anterior wall of the abdomen to mice in the experimental group. Fifteen minutes after either sham treatment or administration of capsaicin, surgical induction of ischemia and reperfusion was performed as described elsewhere herein. The coronary occlusion was maintained for 45 minutes and then released, allowing reperfusion and reestablishing blood flow. Infarct size was determined as described elsewhere herein. In at least one experiment, the area of capsaicin application corresponded to the T10 level in humans.

Example 12

Remote Electrical Inhibition of Ischemia-Related Tissue Damage

Age and gender matched mice were obtained. Experimental and control treated mice were anesthetized, shaved, and electrodes were placed similarly (n=6 mice per group). Fifteen minutes of transcutaneous electrical stimulation (TES) (10 volts, 0.4-0.5 ms pulse width, 100 Hz) was administered to mice in the experimental group. Fifteen minutes after either sham treatment (wire placement but no current) or conclusion of TES, ischemia was induced by coronary occlusion as described elsewhere herein. The coronary occlusion was maintained for 45 minutes and then released, allowing reperfusion and reestablishing blood flow. Infarct size was determined as described elsewhere herein.

Example 13

Remote Electrical Stimulation During Ischemia

Age and gender matched mice were obtained. Experimental and control treated mice were anesthetized, shaved, and electrodes were placed similarly (n=6 mice per group). Ischemia was induced by coronary occlusion as described elsewhere herein. The coronary occlusion was maintained for 30 minutes. Fifteen minutes of transcutaneous electrical stimulation (TES) (10 volts, 0.5 ms, 100 Hz, 400 pulses) was administered to mice in the experimental group. Fifteen minutes after the TES ended, the coronary occlusion was released, allowing reperfusion and reestablishing blood flow. Infarct size was determined as described elsewhere herein. In at least one experiment, the area of electrical stimulation corresponded to the T10 level in humans Example 14

Analysis of Role of C-Fibers in Inhibition of Ischemia-Related Tissue Damage

A relatively selective antagonist of peripheral C-fiber nociceptors, lidocaine, was tested. Ten µl lidocaine (2%) was administered subcutaneously (s.c.) to mice. Subsequently the mice received either a sham treatment or remote electrical stimulation as described elsewhere herein. After 15 minutes, ischemia was induced by coronary occlusion. The occlusion was maintained for 45 minutes prior to reestablishment of blood flow. Pre-treatment with lidocaine reduces the cardioprotective effect of the remote electrical stimulation, such that there is no significant cardioprotection relative to controls. Results from one such experiment are presented in FIG. 2, panel A.

Example 15

Cell Fractionation and Immunoblotting

Mice were euthanized thirty minutes after either sham treatment or abdominal electrical stimulation. Hearts were excised and LV samples (0.5 g) were flash-frozen in liquid nitrogen until used. Frozen tissues were powdered at liquid nitrogen temperature and homogenized in buffer A (5 mM Tris, 4 mM EGTA, 2 mM EDTA, 5 mM dithiothreitol, 1 mM phenylmethylsulfonyl fluoride and EDTA-free protease inhibitor (1 tablet/10 ml)). The homogenate was centrifuged at 100,000×g for 30 minutes at 4° C. The new supernatant was used as the cytosolic fraction: The pellet was re-homogenized with homogenization buffer A containing 1% Triton X, incubated on ice for twenty minutes and then centrifuged at 100, 000×g for 30 minutes at 4° C. The new supernatant was used as the membrane-associated fraction. Protein concentration was determined via a Bio-Rad protein assay (Bio-Rad).

Cytosolic and membrane-associated fractions (50 μg) were electrophoresed on a 10% SDS-PAGE gel. After transfer to membranes, immuno-blotting analysis was performed with PKC isoform specific primary antibodies against PKCα, PKCδ, PKCε and PKCζ (Cell Signaling). The membrane was next incubated with HRP-conjugated secondary mouse (Bio-Rad) or rabbit (Santa Cruz) antibody. Membranes were developed using ECL-PLUS Western blotting Detecting kit (Amersham Pharmacia Biotech) and densitometry of protein bands was quantified using a Fluorchem 880 gel imager. Transfer efficiency and loading equality were examined by staining the membrane with 0.1% Ponceau S in 5% acetic acid. Stained membranes were digitally scanned and densitometric analysis of major bands was used to normalize signal intensity for quantitative analysis as described previously (Liao et al (2007) *J. Mol. Cell. Cardiology* 42(1):106-120 and Brown et al (2005) *Am. J. Physiol.* 289(1):H466-476; herein incorporated by reference in their entirety). Results from one such experiment are presented in FIG. 7.

Example 16

Statistical Analysis

Group size was determined by Power analysis. For parameters that required quantification and evaluation for statistical significance, results were expressed as mean±standard error of the mean (S.E.M.). Statistical significance (probability values) was determined using the Student's t test (two tailed distribution and two sample unequal variance) with the Bonferroni correction. For multiple group comparisons, one way analysis of variance (ANOVA) followed by Fisher post hoc test was used. A P value≤0.05 was considered statistically significant.

Example 17

Assessment of Topical TRPV Family Receptor Agonist Efficacy in Subject Exhibiting Stable Angina (I)

Subjects with chronic stable exertional angina or anginal equivalent who are receiving background medical therapy are identified. Staff conducting and interpreting the exercise tests are blind to the treatment applied to the subject. It is recognized that the burning sensation elicited by capsaicin will not allow the subjects to be blind from the subject's perspective.

Demographics, medical history, limited physical examinations, vital signs, ECG, and concomitant medication history are obtained from prospective subjects. Prospective subjects undergo a small scale capsaicin skin test. Capsaicin cream (0.15%) is applied to a 1×1 $cm^2$ area on the subject's forearm. The reaction and forearm area are observed over the next 30 minutes. Subjects with severe reactions and subjects without a burning sensation (indicating an intact TRPV1 signaling axis) are excluded from the study.

Subjects are randomized. Half the subjects receive a capsaicin treatment at the first visit; half receive a placebo at the first visit. At the second visit, the subject receives the alternate treatment. Subjects are asked to withhold anti-anginal medications the morning of each visit.

Subjects are treated with placebo or topical capsaicin cream (Chattem Inc., 0.035%, 0.10%, or 0.15%) applied over an 8×15 $cm^2$ region centered on the umbilicus (approximately 4 cm anterior and posterior and 7.5 cm left and right of the umbilicus). The cream is applied with gloves and massaged gently into the skin. The staff member applying the cream wears an applicator mask. Thirty minutes (+/−3 minutes) after treatment application, vitals and ECG are repeated. Forty-five minutes (+/−5 minutes) after treatment application, subjects begin an exercise test procedure. Subjects walk as long as they can tolerate, angina-related symptom limited.

Onset of angina or angina-equivalent symptoms, descriptive quality, and intensity are recorded. Study medication is removed with alcohol swabs. Skin is assessed.

In 7 days (+/−1 day) subjects return for the second visit. The procedure is repeated but each subject receives the alternate treatment.

Exercise ECG date is interpreted by a cardiologist according to standard criteria. Images are processed and analyzed using standard laboratory methodology, including computer generated calculations of Summed Stress Score (SSS) and Summed Difference Score (SDS).

Example 18

Assessment of Topical TRPV Family Receptor Agonist Efficacy in Subject Exhibiting Stable Angina (II): Myocardial Perfusion Imaging Subjects are randomized as above. Subjects prepare for each visit as described above. Resting imaging is performed on the subjects. The study medicine is applied as described above herein.

An IV catheter is inserted in conjunction with the exercise test and a radioisotope is administered at rest and post exercise. Exercise tests are performed as described above herein. A Myoview, or Tc-99m Tetrofosmin, scan is performed.

Example 19

Statistical Analysis of Angina Related Efficacy Results

Distributions of endpoints are examined graphically. Data transformations are applied as necessary (e.g. logarithmic transformation of highly skewed data). If apparent violations of parametric assumptions cannot be resolved, non-parametric procedures are applied. All statistical tests and confidence intervals are based on a maximum type I error rate of α=0.05, two-sided.

Analysis of this two-period cross-over design is based on a three-factor repeated measures analysis of variance (ANOVA) model. Treatment (two levels) and study period (two levels) are within-subject factors, while the sequence of treatment administration (two levels) is a randomly assigned between-subjects factor. If a significant carry-over (sequence) effect is observed, all possible estimates of the treatment difference are computed (i.e. between patient-difference in the first period, between patient difference in the second period, within-patient difference in the first sequence, within patient difference in the second sequence), but primacy is given to the between-patient difference in the first period.

Example 20

Duration of Cardioprotective Effect of C-Fiber Stimulation Analysis

Age and gender matched mice were obtained. Experimental and control treated mice were anesthetized, shaved, and electrodes were placed similarly (n=6 mice per group). Fifteen minutes of transcutaneous electrical stimulation (TES) (10 volts, 0.4-0.5 ms, 100 Hz, 400 pulses) was administered to mice in the experimental group. Twenty four hours after either sham treatment or conclusion of TES, ischemia was induced by coronary occlusion as described elsewhere herein. The coronary occlusion was maintained for 30 minutes and then released, allowing reperfusion and reestablishing blood flow. Infarct size was determined as described elsewhere herein. Results from one such experiment are presented in FIG. 12.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

Following from the above description, it should be apparent to those of ordinary skill in the art that, while the methods and kits herein described constitute exemplary embodiments of the present invention, it is to be understood that the inventions contained herein are not limited to the above precise embodiment and that changes may be made without departing from the scope of the invention. Likewise, it is to be understood that it is not necessary to meet any or all of the identified advantages or objects of the invention disclosed herein in order to fall within the scope of the invention, since the invention is defined by the claims and since inherent and/or unforeseen advantages of the claimed methods and kits may exist even though they may not have been explicitly discussed herein.

That which is claimed:

1. A method of inhibiting ischemia-related cardiac tissue damage in a human subject via remote sensory nerve stimulation, the method comprising the steps of:
   (a) identifying a human subject at risk for ischemia-related cardiac tissue damage; and
   (b) topically administering a therapeutically effective transcutaneous electric stimulation to a predetermined region of skin selected from (1) a region of abdominal skin containing sensory nerves from which signal travels to dorsal root ganglia at a thoracic vertebra level at or below the T7 level and encircling the subject and (2) partial regions within said region of abdominal skin containing sensory nerves from which signal travels to dorsal root ganglia at a thoracic vertebra level at or below the T7 level and encircling the subject
   wherein said transcutaneous electric stimulation has a voltage of 1-30 volts and is a pulsing electric stimulation adapted to remotely stimulate a sensory nerve, thereby inhibiting ischemia-related cardiac tissue damage.

2. The method of claim 1, wherein administering said transcutaneous electrical stimulation occurs upon identifying said subject as being at risk for ischemia-related cardiac tissue damage, after identification of an ischemia-related symptom, concomitant with reestablishment of blood flow, or up to three hours after reestablishment of blood flow.

3. The method of claim 2, wherein administering said transcutaneous electrical stimulation occurs within fifteen minutes of the first identification of an ischemia-related symptom.

4. The method of claim 1, wherein the predetermined region consists of a region of abdominal skin containing sensory nerves from which signal travels to dorsal root ganglia at the T9 to T10 thoracic vertebra level and encircling the subject.

5. The method of claim 1, wherein the transcutaneous electric stimulation is applied for a duration of at least about 15 minutes.

* * * * *